United States Patent
Sibley et al.

(12)

(10) Patent No.: US 6,844,190 B2
(45) Date of Patent: Jan. 18, 2005

(54) ST-B17 SEROTONIN RECEPTOR

(75) Inventors: David R. Sibley, Gaithersburg, MD (US); Frederick J. Monsma, Jr., Riehen (CH); Mark Hamblin, Seattle, WA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/829,631

(22) Filed: Apr. 10, 2001

(65) Prior Publication Data

US 2002/0091235 A1 Jul. 11, 2002

Related U.S. Application Data

(63) Continuation-in-part of application No. 08/428,242, filed as application No. PCT/US93/10296 on Oct. 26, 1993, now abandoned, which is a continuation of application No. 07/970,338, filed on Oct. 26, 1992, now abandoned.

(51) Int. Cl.[7] .......................... C12N 5/00; C12N 15/00; C12Q 1/68; C07K 14/435
(52) U.S. Cl. .......................... 435/325; 435/6; 435/69.1; 435/320.1; 536/23.5; 530/350
(58) Field of Search ............................. 536/23.5; 435/6, 435/69.1, 320.1, 325; 530/350

(56) References Cited

U.S. PATENT DOCUMENTS 4,985,352 A  1/1991  Julius et al.
5,472,866 A  12/1995  Gerald et al.

FOREIGN PATENT DOCUMENTS

WO    WO 91/17174    11/1991

OTHER PUBLICATIONS

Hen, R., Of mice and flies: commonalities among 5–HT receptors. Trends in Pharmacological Sciences, 1992, vol. 13, pp 160–165.

Kohen, R., et al., Cloning, characterization, and chromosomal localization of a human 5–$HT_6$ serotonin receptor, J. Neurochemistry, 1996, vol. 66, pp. 47–56.

Monsma, F., et al., Cloning and expression of a novel serotonin receptor with high affinity to tricyclic psychotropic drugs, Mol. Pharm, 1993, 43(3), pp. 320–327.

Ruat, M., et al., A novel rat serotonin (5–$HT_6$) receptor molecular clongin, localization and stimulaton of camp accumulation, BBRC. 1993. vol. 193(1). pp. 268–276.

*Primary Examiner*—Marianne P. Allen
(74) *Attorney, Agent, or Firm*—Knobbe, Martens, Olson & Bear, LLP

(57) ABSTRACT

Genes encoding the St-B17 serotonin receptor protein were cloned and characterized from a rat striatum mRNA and a human genomic library. The St-B17 receptor has nucleotide and amino acid homology with previously described 5-HT genes and can bind ligands that are known to interact with serotonin receptors. In addition, the levels of intracellular cAMP in cells transfected with the receptor gene respond in a dose dependent manner to introduction of serotonin in the media.

12 Claims, 5 Drawing Sheets

ST-B17 SEROTONIN RECEPTOR

RELATED APPLICATIONS

This application is a continuation-in-part and claims the benefit of priority of U.S. patent application Ser. No. 08/428,242, filed Sep. 18, 1995, abandoned, which is the National Stage of International Application No. PCT/US93/10296, filed Oct. 26, 1993, designating the United States of America and published in English as WO 94/10310 on May 11, 1994, which is a continuation-in-part and claims the benefit of priority of U.S. patent application Ser. No. 07/970,338, filed Oct. 26, 1992, abandoned.

SCOPE OF THE INVENTION

This invention relates to cloning and characterization of cellular receptors. Specifically, this invention relates to the cloning and characterization of the St-B17 serotoiin receptor protein.

BACKGROUND

The neurotransmitter serotonin (5-hydroxytryptamine, 5-HT) has a variety of functions in the central nervous system. It has been implicated in many cognitive and behavioral functions, including aggression, sexual behavior, learning and sleep. Disruptions of serotonergic systems may be a critical factor in a number of clinical disorders or conditions including schizophrenia, depression, obsessive compulsive disorder, anxiety, migraine headaches, and pain.

The multitude of effects produced by serotonin are mediated by various serotonin receptors which exist in the central and peripheral nervous system. The transduction of serotonergic signals across the neuronal membrane is mediated by a diversity of receptor subtypes which, in mammals, appear to fall into four pharmacologically distinct classes designated 5-$HT_1$–5-$HT_4$. The $5HT_1$ subcategory has been further subdivided into five different subtypes referred to as $5HT_{1A-E}$. The primary structures for a number of these receptors have been elucidated by molecular cloning, including the 5-$HT_1$, 5-$HT_2$ and $5HT_3$ subclasses. In addition, the sequences of three different Drosophila serotonin receptors, 5-$HT_{dro1}$ and 5-$HT_{dro2A,B}$, have been reported.

Selective therapeutic agents, including agonist and antagonist drugs, have been developed based on serotonin receptor technologies. 5-$HT_2$ antagonists, for example, are useful in the treatment of schizophrenia, parkinsonism, and anxiety disorders. Several azapirones, such as buspirone, gepirone, and ipsapirone, have high affinities for $5HT_{1A}$ receptors in the brain, and are useful in the treatment of anxiety. Highly selective 5-HT uptake inhibitors, which have minimal effects on norepinephrine or dopamine uptake or on other neurotransmitter receptors, have been used to successfully treat depression.

Characterization of all specific 5-HT receptors would clarify the role of serotonin in the central nervous system. Analysis of the receptor subtypes and their functional role in the central nervous system would help elucidate the pathophysiological basis of many human diseases. Accordingly, there is a need for identification and characterization of all specific 5-HT receptors, and the development of selective therapeutic agents based on these receptor technologies.

SUMMARY

Figure 1:
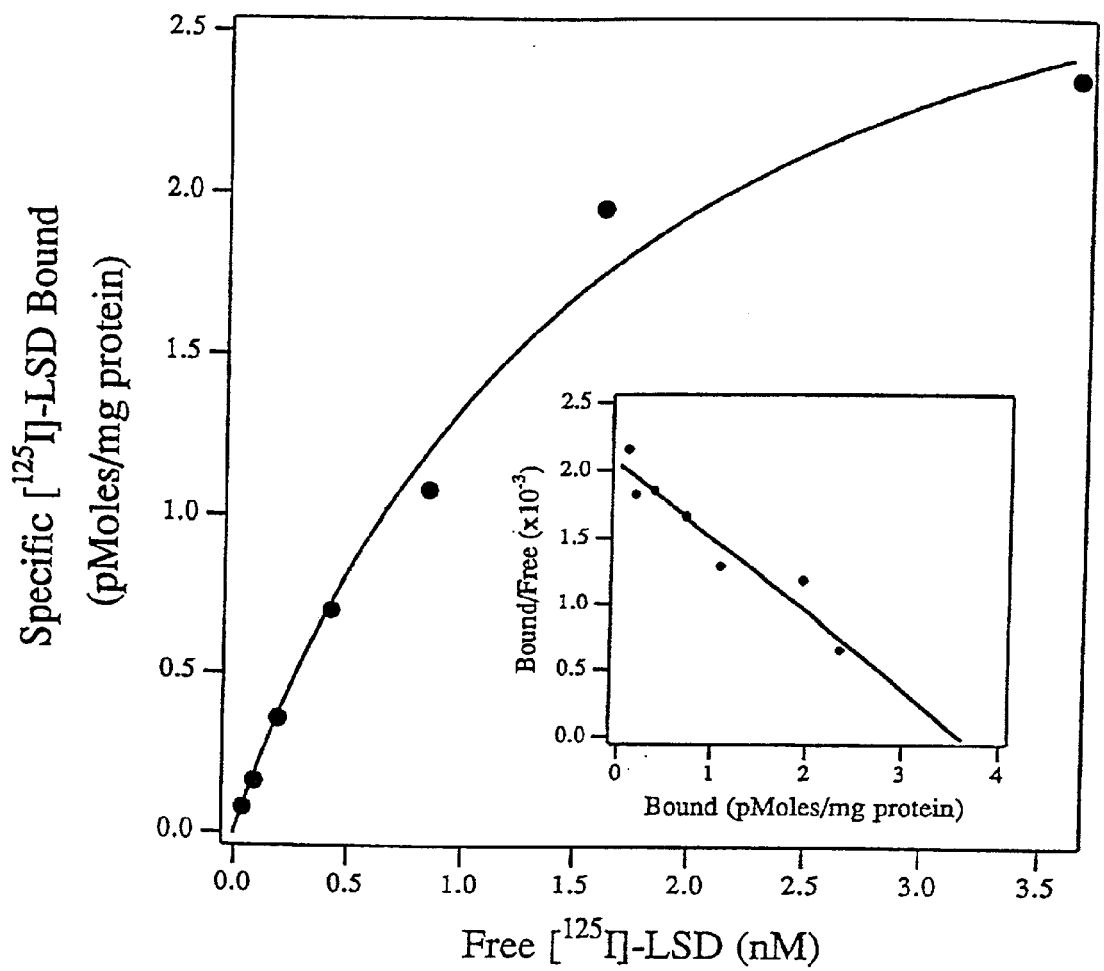
FIG. 1: Saturation analysis of specified [$^{125}$I]-LSD binding to membranes prepared from Cos-7 cells transiently transfected with construct pSRα-B17. The experiment shown is representative of 3 independent experiments conducted in triplicate. Inset, scatchard analysis of saturation binding data. In this experiment the $K_D$ and $B_{max}$ values were 1.5 nM and 3.4 pMoles mg protein$^{-1}$, respectively.

In this application the nomenclature announced in Kohen et al., J. Neurochem. 66: 47–56 (1996) is to be used, e.g., St-B17 is to be designated 5-$HT_6$.

One embodiment of the present invention is the isolated mammalian serotonin receptor protein St-B17. Preferably this receptor protein is human. The present invention also encompasses species variations of the St-B17 receptor.

Another embodiment of the present invention is a method for screening a drug candidate for central nervous system activity by contacting the drug candidate with the St-B17 protein and measuring binding of the drug candidate by the protein.

An additional embodiment of the present invention is a method for screening a drug candidate for central nervous system activity by first contacting the St-B17 serotonin receptor protein with a first molecule known to be bound by the protein to form a first complex of the protein and the first molecule; then contacting the first complex with the drug candidate; and finally measuring whether the drug candidate displaces the first molecule from the first complex. This method can preferably include in the measuring step, the step of measuring the formation of a second complex of the protein and the drug candidate. An alternative method of measuring the displacement of the first molecule can be performed by measuring the amount of the first molecule that is not bound to the protein.

A further embodiment of the present invention includes a recombinant construct of the polynucleotide, preferably the polynucleotide of SEQ ID NO: 7, encoding the St-B17 serotonin receptor protein operably linked to a heterologous promoter.

Another embodiment of the present invention is directed at the polynucleotide sequence encoding the St-B17 receptor. Preferably, this polynucleotide sequence is Sequence ID NO: 7 or species variations thereof. Additionally, the present invention encompasses an isolated nucleotide sequence having homology to at least 18 contiguous nucleotides of the St-B17 gene.

The present invention also embodies a mammalian cell line, preferably human, in continuous culture expressing the St-B17 serotonin receptor protein. Particularly, the cell line contains the polynucleotide Sequence ID NO: 7 or species variations thereof. One especially preferred embodiment includes HEK 293 cells in continuous culture expressing the St-B17 receptor.

Yet another embodiment of the present invention includes isolated antibodies against the St-B17 serotonin receptor protein. Preferably these isolated antibodies are polyclonal, even more preferably, the isolated antibodies are monoclonal.

An even further embodiment of the present invention includes a method of screening a ligand for binding to the St-B17 serotonin receptor by the steps of:

transfecting a cell line with a gene encoding the St-B17 serotonin receptor protein in an expression vector;

culturing the cell line to express the gene in media containing a ligand of the receptor; and measuring the binding of the ligand the receptor produced by the cell line.

Preferably, in this method, the cell line is from a mammal, more preferably a human, and most preferably the cell line is HEK 293. An additional preferred embodiment of the above method entails transfecting cells with the St-B17 serotonin receptor encoded by the polynucleotide of SEQ ID NO: 7. Additional preferred embodiments of this method include using eukaryotic expression vectors, preferably pSRα-B17. Another preferred embodiment includes using ligands that are labeled and the label is either radioactive or calorimetric.

Still another embodiment of the present invention is a method of determining the ability of a drug to inhibit ligand binding to the St-B17 serotonin receptor protein by the following steps:

transfecting a cell line with a DNA sequence encoding St-B17 in an expression vector;

culturing the cell line to express the St-B17 receptor in media containing a ligand of the receptor;

determining the level of binding of the ligand to the receptor;

culturing the same cell line to express the receptor in the presence of both the ligand and the drug; and determining the level of binding of the ligand to the expressed receptor, wherein a lower level of binding in the presence of the drug indicates that the compound is an inhibitor of ligand binding.

Preferably, the cell line of this method is mammalian, most preferably HEK 293, and the ligand, the drug or both are labeled. Additionally, the expression vector of this method can preferably be pSRα-B17 and the ligand can advantageously be serotonin.

Yet another embodiment of the present invention is a method for determining the ability of a drug to inhibit ligand binding to the St-B17 serotonin receptor by the following steps:

transfecting a cell line with a gene encoding the St-B17 receptor protein in an expression vector;

culturing the cell line to express the receptor;

determining the level of binding of the ligand to the receptor;

culturing the same cell line to express the receptor in the presence of both the ligand and the drug being tested for inhibition; and determining the level of cAMP accumulation in the cell, wherein a lower level of cAMP accumulation in the cell in the presence of the drug indicates inhibition of ligand binding.

Still another embodiment of the present invention is a method of determining the ability of a drug to inhibit ligand binding to the St-B17 serotonin receptor protein by the steps of:

transfecting a cell line with a DNA sequence encoding St-B17 in an expression vector;

culturing the cell line to express the St-B17 receptor in media containing a ligand of the receptor;

isolating the membranes from the cell line, wherein the membranes contain the expressed St-B17 receptor;

determining the level of binding of the ligand to the receptor on the membranes;

incubating the membranes in the presence of both the ligand and the drug; and determining the level of binding of the ligand to the membranes, wherein a lower level of binding in the presence of the drug indicates that the compound is an inhibitor of ligand binding.

Still another embodiment of the present invention is a method for detecting expression of the St-B17 serotonin receptor gene in a tissue sample by the steps of:

removing a tissue sample from a mammal;

contacting the mRNA in the cytoplasm of the tissue sample with a labeled polynucleotide probe having homology to the St-B17 serotonin receptor gene; and detecting the binding of the probe to the tissue wherein positive binding indicates expression of the St-B17 serotonin receptor gene.

DETAILED DESCRIPTION

We have cloned a new serotonin 5-HT (St-B17) receptor gene from rat and human brain cells. This receptor has a nucleotide sequence that is distinct from any previous gene in the serotonin family. The rat St-B17 gene has a 1311 bp open reading frame coding for a protein with 437 amino acids. The human St-B17 gene has a 1320 bp open reading frame coding for a protein with 440 amino acids.

In addition, this receptor protein exhibits a distinct pharmacological profile not previously described. The unique pharmacology together with the relatively low level of homology (<50%) of St-B17 with previously cloned 5-HT receptor subtypes indicates that this receptor does not belong to any of the previously defined $5\text{-HT}_1$–$5\text{-HT}_4$ subcategories of 5-HT receptors. Thus, St-B17 represents an unknown and uncharacterized receptor.

The molecular cloning of St-B17 will be useful for developing drugs which interact with 5-HT receptors. For instance, the cloning of this novel gene allowed us to develop new assays for discovering serotonin receptor binding and inhibitory drugs. These assays were performed by transfecting cells, such as Cos-7 mammalian cells, with the gene encoding the St-B17 serotonin receptor protein in an expression plasmid. The Cos-7 cells were then placed in media and expressed the St-B17 receptor on their cell surface. Radiolabeled ligands were then tested for binding to these transfected cells.

By using this method we were able to screen many drugs for their binding activity to the serotonin receptor. Similarly, this assay system was used to detect competitive inhibitors of serotonin binding. By incubating the transfected cells in the presence of a radiolabeled known binding molecule (LSD) we were able to test various drugs for their ability to inhibit this binding. Table 1 below describes a suite of drugs that had wide-ranging affects on $^{125}$I-LSD binding to the rat St-B17 serotonin receptor.

Since serotonin binding is intimately involved in the functionality of the central nervous system, assays for detecting drugs which bind or block serotonin receptors are of paramount importance. As discussed in the background, many behavioral functions are believed to be mediated through serotonergic systems. For researchers to be able to accurately assess the projected effects of a new serotonin-related drug in humans, it is important to test that drug's effect on every known serotonin receptor. The discovery of the St-B17 receptor provides the researcher with a previously unknown assay to study possible in vivo effects of the drug being tested.

It is also anticipated that isolated St-B17 receptor protein will be useful for performing assays to determine agents which bind or inhibit binding to serotonin receptors. In discussing the isolated St-B17 receptor protein, we are referring to not only affinity-purified protein, but also receptor proteins bound in a membrane and removed from the cell. For example, we transfected Cos-7 cells with the gene encoding the St-B17 receptor protein in an expression plasmid. After incubation in media to allow St-B17 receptor expression the cells were lysed and the membranes (containing the bound St-B17 receptors) were pelleted. These membranes, isolated from the host cells were used for radiolabeled ligand binding studies.

The present invention includes isolated St-B17 serotonin receptors from rats, humans, other mammals, and other vertebrates. Further investigations of St-B17's role in vivo and in vitro will help improve current therapies for several neuropsychiatric disorders by providing additional information on each drug's receptor-mediated action.

For the first step in cloning the St-B17 receptor we used the polymerase chain reaction (PCR) to selectively amplify cDNA sequences from mRNA purified from rat corpus striatum. Poly(A)$^+$ RNA from the rat striatum was used to first synthesize a cDNA library by reverse transcription using methods well known in the art. The following example shows one method for amplifying the serotonin receptor genes using PCR amplification.

EXAMPLE 1

PCR Amplification of Rat Striatum mRNA

We used a pair of highly degenerate primers, with sequences which were derived from the third and sixth transmembrane (TM) regions of previously cloned G protein-linked receptors in multiple rounds of PCR to amplify the serotonin gene sequences in the striatum library.

Polymerase chain reaction amplification was carried out as previously described (Monsma, F. J., Jr., Mahan, L. C., McVittie, L. D., Gerfen, C. R. & Sibley, D. R., *Proc. Natl. Acad Sci. USA* 87, 6723–7 (1990)) using cDNA prepared from rat striatal mRNA and 1 $\mu$M each of the following primers:

```
5'-GTCGACCCT(GT)T(GT)(CG)GCC(AC)TCA(GT)CA(TC)(GA)G(AG)-TCGCTA-3'   SEQ ID NO: 1

5'-AAGCTTATGAA(AG)AAGGGCAG(GC)CA(AG)CAGAGG(GT)(CT)-(AG)(CA)A- 3'.  SEQ ID NO: 2
```

The PCR timing cycle was 1.5 min at 93° C., 2 min at 50° C., and 4 min at 72° C. followed by a 7 min extension at 72° C. The reaction products were purified and size fractionated on a 1% agarose gel. Individual bands were excised, electroeluted, concentrated by ultrafiltration, and ligated into the pCR1000© vector (INVITROGEN). Competent INVaF bacterial cells (INVITROGEN) were transformed and mini-preparations of plasmid DNA prepared for insert sequencing.

This process resulted in the amplification of several cDNA fragments ranging from 300 to approximately 500 base pairs (bp) in size. Each fragment was preliminarily characterized by DNA sequence analysis. Several of these cDNA fragments exhibited sequence homology with previously cloned G-protein coupled receptors such as serotonin, one of which, clone St-B17$_1$ (538 bp), was particularly homologous with several catecholamine receptors and was thus selected for further characterization.

We selected 1×10$^6$ recombinants from the rat striatal cDNA library, constructed in the λ ZAP II© vector (STRATAGENE, La Jolla, Calif.), to be screened with the 538 bp St-B17$_1$ PCR fragment. The 538 bp fragment was made into a probe by $^{32}$P-labeling (via nick translation) using well known methods. Duplicate nitrocellulose filters were hybridized in 50% formamide, 0.75 M NaCl, 0.075 M sodium citrate (5×SSC), 5× Denhardt's solution 0.02 M $Na_2HPO_4$, 0.25% SDS, 0.15 mg/ml salmon sperm DNA, and 4×10$^6$ dpm/ml of $^{32}$P-labeled probe for 24 hr at 37° C. High stringency washing of the filters was performed with 1×SSC and 0.1% SDS at 65° C. prior to autoradiography.

The λ phage found to hybridize with the probe were subsequently plaque purified. In vivo excision and rescue of the nested pBluescript plasmids from the λ ZAP II clones was performed using helper phage according to the STRATAGENE protocol.

Briefly, the λ phage carry a nested pBluescript plasmid which can be excised via the STRATAGENE protocol. This nested plasmid carried the St-B17 gene and could be used for subsequent sequencing and transfection. Nucleotide sequence analysis was performed using the Sanger dideoxy nucleotide chain termination method with Sequenase© (US BIOCHEMICAL CORP.) on the excised denatured double-stranded plasmid templates.

One positive clone (St-B17$_2$) from the above screening, containing a cDNA insert of 2.8 kb, was isolated and nucleotide sequenced. The largest open reading frame was 879 bp long encoding a protein containing sequences homologous to transmembrane (TM) regions I–VI of previously cloned biogenic amine receptors.

Further analysis of the 2.8 kb cDNA revealed the presence of a sequence 210 bp beyond the end of the open reading frame which was homologous to the seventh transmembrane (TM) region of several receptors. Careful examination of the DNA sequence between these putative TM regions VI and VII revealed the presence of consensus donor and acceptor sequences for intron/exon splice junctions suggesting the possibility that this region represented an un-spliced intron having an inframe stop codon. Sequence ID NO: 9 is a partial polynucleotide sequence of the 2.8 kb clone having the entire coding sequence, and the internal intron. The amino acid sequence corresponding to the first coding region of SEQUENCE ID NO:9 is shown as SEQUENCE ID NO:10. The amino acid sequence corresponding to the second coding region of SEQUENCE ID NO:9 is shown as SEQUENCE ID NO:11.

This would explain the homology to the seventh TM region in the purported non-coding portion of the gene. The possibility that we had isolated a cDNA from a partially spliced mRNA was examined, as described in Example 2 below, using PCR to amplify this putative intron region from cDNA prepared from rat striatal mRNA.

EXAMPLE 2

Amplification and Analysis of the 2.8 kb Insert

Primers P3 and P4 were synthesized to have homology near to the 3' and 5' ends of the putative splice region. The sequence of primer P4 is complementary to the coding sequence since it was designed to anneal with the homologous DNA strand. With these primers, we would either isolate 223 bp sequences corresponding to a spliced message, or 416 bp sequences corresponding to an unspliced message. This system could thereby indicate if the putative intron acceptor/donor sites were really utilized for splicing reactions in the cell.

| PRIMER | SEQUENCE | SEQ ID NUMBER |
|---|---|---|
| P3 | AAGCATAGCA GGAAGGCCTT GAAGGCCAGC CTG | SEQ ID NO: 3 |
| P4 | GGCGAGAAAT ACGCCCTGAA GTTCTCCCGG GAC | SEQ ID NO: 4 |

Amplification across the putative splice region with primers P3 and P4 resulted in a primary DNA product of 223 bp, the size predicted for mRNA spliced at the observed donor/acceptor sites, and a minor band of 416 bp, the size expected based on the sequence of the unspliced St-B17$_2$ cDNA clone. We thus believed that the St-B17$_2$ cDNA clone was derived from a minor, incompletely spliced mRNA.

Since an additional screen of the cDNA library did not result in the isolation of a full-length, completely spliced clone, we used PCR following the protocol outlined in Example 1 to amplify the predicted coding sequence from rat striatal mRNA.

EXAMPLE 3

Amplification of Putative Coding Region

We used primers P1 and P2 (shown below as SEQ ID NOS: 5 and 6, respectively) and PCR to amplify the 2.8 kb clone isolated in Example 2 from the rat striatum cDNA library. Primer P2 was complementary to the coding sequence since it was designed to hybridize with the homologous nucleotide strand.

| PRIMER | SEQUENCE | SEQ ID NUMBER |
|---|---|---|
| P1 | TTGCCAATAC TACTCTAAGG TGCAGCTTCC | SEQ ID NO: 5 |
| P2 | CACACGACTT AACTCCATAG AGTCGATCGG | SEQ ID NO: 6 |

Two nucleotide sequences of 1.6 and 1.4 kb were obtained from the PCR reaction, the latter of which (St-B17$_3$) was subcloned into plasmid pBluescript II© SK (+). Sequence analysis confirmed the identity of St-B17$_3$ and revealed that the putative intron was absent in this clone (SEQ ID NO: 7) with the flanking exons spliced together at nucleotide 873 as predicted. Splicing at this position resulted in a 1,311 bp open reading frame encoding a protein of 437 amino acid residues (SEQ ID NO: 8) with a calculated molecular weight of 46.8 kD.

Hydropathy analysis of the deduced amino-acid sequence of the spliced St-B17$_3$ protein indicated seven hydrophobic regions predicted to represent putative transmembrane spanning domains. When compared to previously cloned G-protein coupled receptors, the transmembrane regions of St-B17 exhibited high homology to various serotonin (5-HT) receptors suggesting that it may be a member of this receptor family.

Within the transmembrane regions, St-B17$_3$ exhibited homologies of 41%, 40%, 39%, 38%, 37% and 36% with 5-HT$_2$, 5-HT$_{1D}$, 5-HT$_{1C}$, 5-HT$_{1B}$, 5-HT$_{1A}$ and 5-HT$_{1E}$ receptors, respectively. The third cytoplasmic loop of St-B17$_3$, consisting of 57 residues, would be the shortest of the cloned 5-HT receptors, though similar in length to the 5-HT$_{1C}$ and 5-HT$_2$ receptors. These receptors have been described previously by Julius, D. et al., *Science* 241, 558–564 (1988); and Julius, D. et al., *Proc. Natl. Acad. Sci. USA* 87, 928–932 (1990); and Pritchett, D. B., et al., *EMBO J.* 7, 4135–4140 (1988). Similarly, while the 117 residue carboxy-terminal tail of St-B17$_3$ is the longest amongst the 5-HT receptors, it is similar in length to that found in the 5-HT$_{1C}$ and 5-HT$_2$ receptors.

The combination of a relatively short third cytoplasmic loop and a long carboxy-terminus is common among receptors which are coupled to the stimulation of either the adenylyl cyclase or phospholipase C signal transduction systems. St-B17$_3$ also contained one potential N-linked glycosylation site at Asn-9 in the extracellular amino terminus. Additionally, several potential sites for phosphorylation by the cyclic AMP-dependent protein kinase or protein kinase C in both the third cytoplasmic loop and the intracellular carboxy-terminal tail were deduced.

To definitively establish the identity of the receptor encoded by St-B17$_3$, we wanted to express this gene in mammalian cells. Unfortunately, the PCR-amplified full-length, correctly spliced St-B17$_3$ cDNA could not be used directly for expression due to several PCR-generated base substitutions in the 5' region up-stream of the internal Bam H1 site.

We thus constructed a hybrid cDNA in which the entire 3' sequence down-stream of the Bam H1 site from the intron-containing clone (St-B17$_2$) was replaced with the corresponding Bam H1 fragment from the correctly spliced, PCR-amplified cDNA (St-B17$_3$) as explained below in Example 4.

EXAMPLE 4

Construction of Expression Clone

We cleaved the 1.4 kb St-B17$_3$ clone isolated in Example 3 with BamHI by well known methods. We also cleaved the 2.8 kb St-B17$_2$ clone isolated in Example 1 with BamHI. By mixing and annealing the fragments from these two digestions, we derived a clone (St-B17) with the 5' end of St-B17$_2$ and the 3' end of St-B17$_3$. The resultant fusion gene had a functional 5' leader and initiation codon, and a correctly spliced intron/exon junction.

This construct was subcloned into the eucaryotic expression vector pCD-Srα yielding pSRα-B17. This clone was then used to transfect mammalian cells to study the expression, binding, and regulation of the new serotonin receptor gene as discussed below in Example 5.

EXAMPLE 5

Transfection of Mammalian Cells with St-B17

Transient transfection of Cos-7 cells with pSRα-B17 resulted in the appearance of high affinity and saturable binding sites for the serotonergic ligand [$^{125}$I]-LSD (lysergic acid diethylamide).

Cos-7 cells were transfected with the pSRα-B17 construct using the calcium phosphate precipitation method as previously described by Monsma, F. J. et al., *Proc. Natl. Acad. Sci. USA* 87, 6723–7 (1990). Cells were harvested 72 hours after transfection and either disrupted in a dounce homogenizer in 50 mM Tris-HCl, pH 7.4 at 37° C., 10 mM MgSO$_4$ and 0.5 m M EDTA, or frozen in 5 mM Tris-HCl, pH 7.4 at 25° C., 5 mM MgCl$_2$, 250 mM sucrose and stored in liquid N$_2$ prior to membrane preparation. Crude membranes were prepared from cell homogenates by centrifugation at 43,000×g, and re-suspension in homogenization buffer at a protein concentration of 60 μg/ml.

Once the crude membranes had been prepared from the cell homogenates, we proceeded to pharmacologically screen various drugs for their effect on [$^{125}$I]-LSD to St-B17 as discussed below in Example 6.

EXAMPLE 6

Pharmacological Screening Assays Using St-B17

It was first necessary to determine the binding strength and saturation point of LSD, so that we could later analyze drugs that displaced this chemical. Radiolabeled LSD ([$^{125}$I]-LSD) exhibited a dissociation constant (K$_D$) of 1.26 (±0.17, n=3) nM and maximum binding (B$_{max}$) values ranging from 2–5 pMoles/mg protein (FIG. 1) when added to the membranes prepared by the method of Example 5. FIG. 1 shows the saturation analysis of [$^{125}$I]-LSD binding to membranes prepared from Cos-7 cells transiently transfected with construct pSRα-B17. The experiment reported is representative of 3 independent experiments conducted in triplicate. The inset (FIG. 1) is a scatchard analysis of the saturation binding data. In this experiment the K$_D$ and B$_{max}$ values were 1.5 nM and 3.4 pMoles mg protein$^{-1}$, respectively. This assay shows the strong binding of LSD to the St-B17 receptor.

Figure 2:
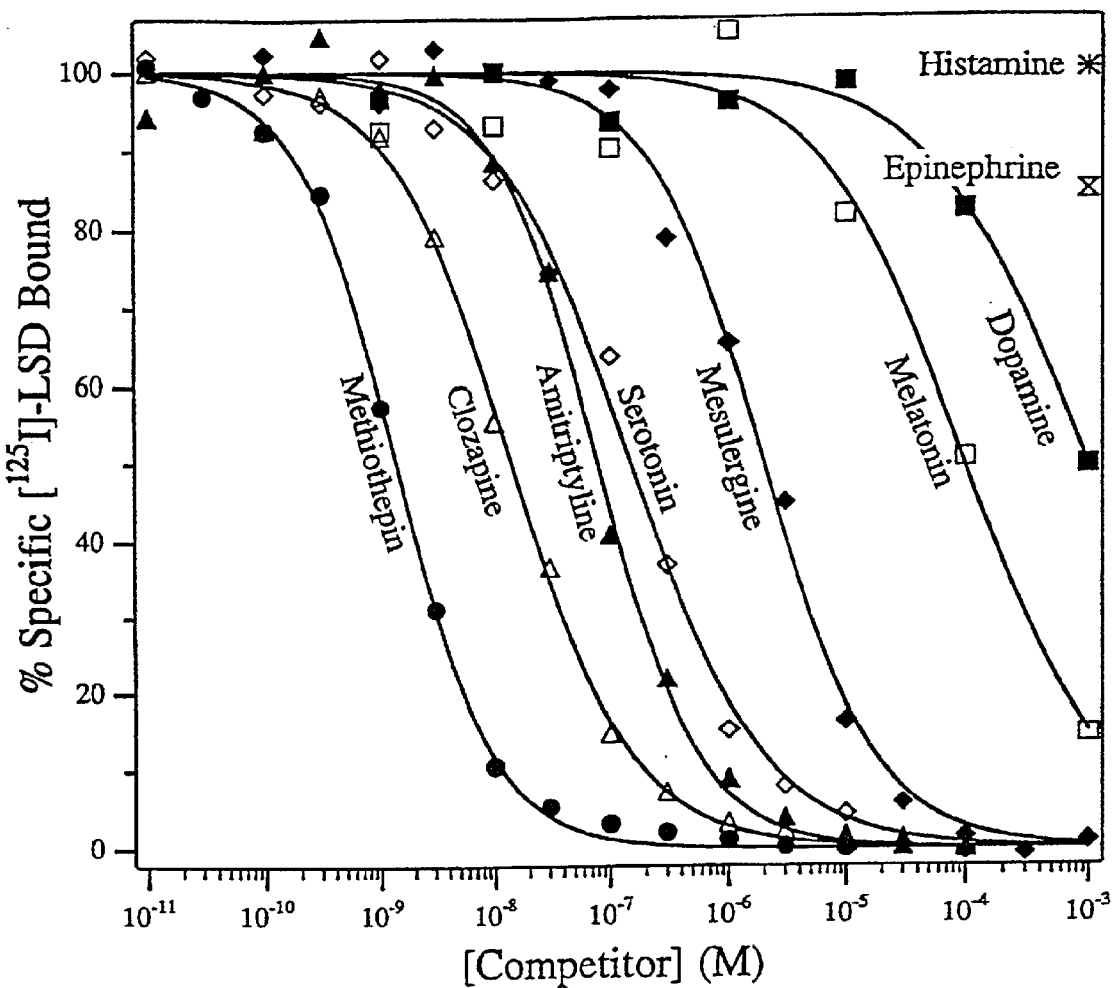
FIG. 2: Pharmacological analysis of [$^{125}$I]-LSD binding to Cos-7 cell membranes expressing clone St-B17. Competition curves shown are representative of 3 independent experiments conducted in triplicate.

FIG. 2 displays the results of a pharmacological competition assay to analyze the displacement of [$^{125}$I]-LSD in the presence of various serotonin receptor binding drugs. This experiment was performed on Cos-7 cell membranes expressing the St-B17 serotonin receptor. The competition curves shown are representative of 3 independent experiments conducted in triplicate. Average inhibition constants (K$_i$) and SEM values are given in Table 1. No specific binding of [$^{125}$I]-LSD was observed in untransfected Cos-7 cells or in cells transfected with the pCD-Srα expression vector alone (controls).

TABLE 1

Pharmacology of St-B17 Expressed in Cos-7 Cells

| Drug | K$_i$ (nM) Mean ± SEM vs. [$^{125}$I]-LSD | vs. [$^3$H]-5-HT |
|---|---|---|
| Methiothepin | 1.84 ± 0.23 | 0.39 ± 0.063 |
| Lisuride | 8.19 ± 0.48 | 5.3 ± 1.3 |
| Clozapine | 12.87 ± 1.69 | 20 ± 2.5 |
| Dihydroergotamine | 13.07 ± 0.90 | 5.4 ± 5.4 |
| 2-Br-LSD | 17.14 ± 1.11 | |
| Pergolide | 29.87 ± 7.31 | |
| Metergoline | 29.97 ± 0.38 | 61 ± 23 |
| Amoxipine | 30.40 ± 1.64 | |
| Lergotrile | 36.45 ± 1.04 | |
| 5-methoxytryptamine | 38.92 ± 3.95 | 18 ± 2 |
| Ritanerin | 44.12 ± 4.35 | 16 ± 2 |
| Mianserin | 45.74 ± 8.93 | 38 ± 7 |
| Clomiprimine | 53.78 ± 3.28 | |
| 5-Hydroxy-N,ω-methyltryptamine | 57.95 ± 8.32 | |
| Loxapine | 64.75 ± 0.60 | 56 ± 1.5 |
| Amitriptyline | 69.64 ± 7.21 | 82 ± 6 |
| N,N-Dimethyl-5-methoxytryptamine | 79.81 ± 3.86 | |
| 1(1-naphthyl)piperazine | 103.61 ± 13.81 | |
| 5-Benzyloxytryptamine | 110.18 ± 17.90 | |
| Cyproheptadine | 133.85 ± 6.17 | |
| Doxepin | 135.74 ± 7.11 | |
| Nortriptyline | 147.49 ± 2.61 | |
| 5-HT | 151.01 ± 12.78 | 56 ± 9 |
| Dihydroergocryptine | 160.70 ± 13.21 | |
| Imipramine | 208.49 ± 22.76 | 190 ± 3 |
| N,ω-Methyltryptamine | 341.60 ± 32.21 | |
| MethyscrGide | 371.74 ± 72.66 | |
| Tryptamine | 438.27 ± 14.84 | |
| TFMPP | 482.37 ± 37.21 | |
| CGS 12066B | 737.69 ± 66.63 | |
| 5-Carboxamidotryptamine | 774.35 ± 84.39 | 253 ± 20 |
| PAPP | 805.62 ± 75.17 | |
| Mesulergine | 1718.88 ± 248.35 | |
| Fluoxetine | 1765.36 ± 290.37 | |
| mCPP | 2309.60 ± 343.05 | |
| 2-MPP | 3054.95 ± 321.06 | |

Increasing concentzations of the indicated compounds were used to inhibit the binding of either 0.5 nM [$^{125}$I]-LSD or 5 nM [$^3$H]-5-HT to membranes of Cos-7 cells transiently transfected with clone St-B17. [$^{125}$I]-LSD competition assays were performed by incubating the transfected Cos-7 cells with [$^{125}$I]-LSD and the indicated concentrations of each drug as described above and in FIG. 2, while those for [$^3$H]-5-HT were performed as previously described (Hamblin, M. W. & Metcalf, M. A., *Mol. Pharmacol.* 40, 143–148 (1991)). K$_i$ values were obtained from graphically determined IC$_{50}$ values by the method of Cheng and Prussoff (*Biochem. Pharmacol.* 22, 3099–3108 (1973)) and are presented as the geometric mean±SEM (n=3) calculated according to De Lean et al. (*Mol. Pharmacol.* 21, 5–16 (1982)).

This method thereby provides a way of screening drug candidates for central nervous system activity by testing its binding to isolated St-B17. We believe that drugs which bind to the St-B17 receptor in vitro will also have effects in vivo. In addition to directly measuring the binding of a drug to the St-B17 receptor, we were also able to measure the displacement of known binding ligands to the St-B17 receptor. By measuring the binding of a ligand as discussed above, and then comparing that binding to the level of binding in the presence of a drug candidate, we were able to estimate the potential of the drug to displace the ligand.

The following compounds were screened and found to exhibit inhibition constant (K$_i$) values>10 μM: zimelidine, zacopride, NAN-190, citalopram, BIMU 1, metoclopromide, fenfluramine, MDL 72222, 8-OH-DPAT, BRL 24924, BRL 43694A, GR 38032F, ICS 205,930, ketanserin, melatonin, spiroperidol, tyramine, DAU 6215, DAU 6285, dopamine, epinephrine, histamine, idazoxan, LY 278,584, maxindol, norepinephrine, octopamine, paroxetine, and pindolol.

Preliminary characterization of the St-B17 pharmacology indicated that amongst several endogenous biogenic amines, including dopamine, melatonin, epinephrine, norepinephrine or histamine, only 5-HT (serotonin) was capable of completely displacing [$^{125}$I]-LSD binding, exhibiting a $K_i$ of 150 nM (FIG. 2 and Table 1). The Hill coefficient for the 5-HT competition curve was not significantly different from unity and the affinity of 5-HT was not influenced by addition of the guanine nucleotide analogue GppNHp.

The binding of 5-HT to St-B17 was also investigated directly using [$^3$H]-5-HT as the radioligand. Saturation analysis of [$^3$H]-5-HT binding revealed the presence of a single class of high affinity, saturable binding sites in transfected, but not untransfected, Cos-7 cells. Analysis of the [$^3$H]-5-HT saturation binding data revealed a $K_D$ of 37 (±5.0, n=3) nM and $B_{max}$ values of 1–3 pMoles/mg protein. The binding of [$^3$H]-5-HT was similarly not affected by the addition of guanine nucleotides. These initial binding data would thus suggest that St-B17 encodes a 5-HT receptor subtype.

Further characterization of the St-B17 pharmacology involved the utilization of a variety of drugs which are known to exhibit specificity for various serotonergic receptor subtypes and other binding sites. The average $K_i$ values for compounds competing with better than 10 μM affinity are shown in Table 1 with representative competition curves for [$^{125}$I]-LSD binding shown in FIG. 2.

Examination of the rank order of potency for a variety of serotonergic agents reveals that the pharmacology of clone St-B17 does not correspond to any previously described serotonin receptor subtype. A number of drugs selective for 5-HT$_3$ and 5-HT$_4$ receptors (i.e., MDL 72222, ICS 205,930, or DAU 6285) exhibit virtually no affinity for St-B17, while agents selective for other 5-HT receptor subtypes such as 8-OH-DPAT (5HT$_{1A}$), CGS 12066B (5-HT$_{1B}$), mesulergine (5-HT$_{1C}$), or ketanserin (5-HT$_2$) bind with relatively low affinity. Ergot alkaloids, especially ergoline derivatives (i.e., LSD, lisuride, or pergolide), display relatively high affinity for St-B17 as does the non-selective serotonergic antagonist methiothepin.

Interestingly, the atypical and typical anti-psychotics clozapine and loxapine, respectively, also exhibited high affinity for St-B17, as did several tricyclic anti-depressant drugs (i.e., amoxipine, clomiprimine, and amitriptyline) which all had $K_i$ values under 100 nM. In general, the drugs which exhibited the greatest affinity for St-B17 (i.e., $K_i$<100 nM) were tricyclic, ergoline or tryptamine derivatives.

Competition for [$^3$H]-5-HT binding by a number of drugs revealed, with a few exceptions, the same rank order of potency as for inhibition of [$^{125}$I]-LSD binding (Table 1). However, for some drugs the $K_i$ values determined by competition with [$^3$H]-5-HT were up to 5-fold lower than those determined by competition with [$^{125}$I]-LSD, with the exception of clozapine, metergoline and amitriptyline, which exhibited somewhat greater potency in competition with [$^{125}$I]-LSD.

Although the pharmacological profile of St-B17 did not correspond to previously defined 5-HT receptor subtypes, it did resemble the profile described by Conner and Mansour for 5-HT stimulation of adenylyl cyclase activity in the NCB-20 neuroblastoma cell line (*Mol. Pharmacol.* (1990) 37, 742–751). In these cells 5-HT activated adenylyl cyclase with an EC$_{50}$ of 300 nM and a variety of tryptamine derivatives exhibit EC$_{50}$ values similar to their $K_i$ values for inhibition of [$^{125}$I]-LSD binding to St-B17. Similarly, antagonism of 5-HT-stimulated adenylyl cyclase activity in NCB-20 cells by a variety of compounds, including methiothepin, mianserin, amitriptyline, and cyproheptadine, also exhibited apparent $K_i$ values and a rank order of potency similar to those observed for inhibition of [$^{125}$I]-LSD binding to St-B17.

It is contemplated that other means of labeling LSD or the other tested drugs would also provide an assay for the inhibition of compounds such as that discussed above. LSD could be labeled either radioactively or colormetrically and still provide the desired assay.

The distribution of mRNA encoding St-B17 was evaluated by Northern blot analysis of poly (A+) RNA prepared from a variety of rat brain regions as well as other peripheral tissues. The results from these experiments are shown below in Example 7.

EXAMPLE 7

Distribution of mRNA Encoding St-B17

Figure 3:
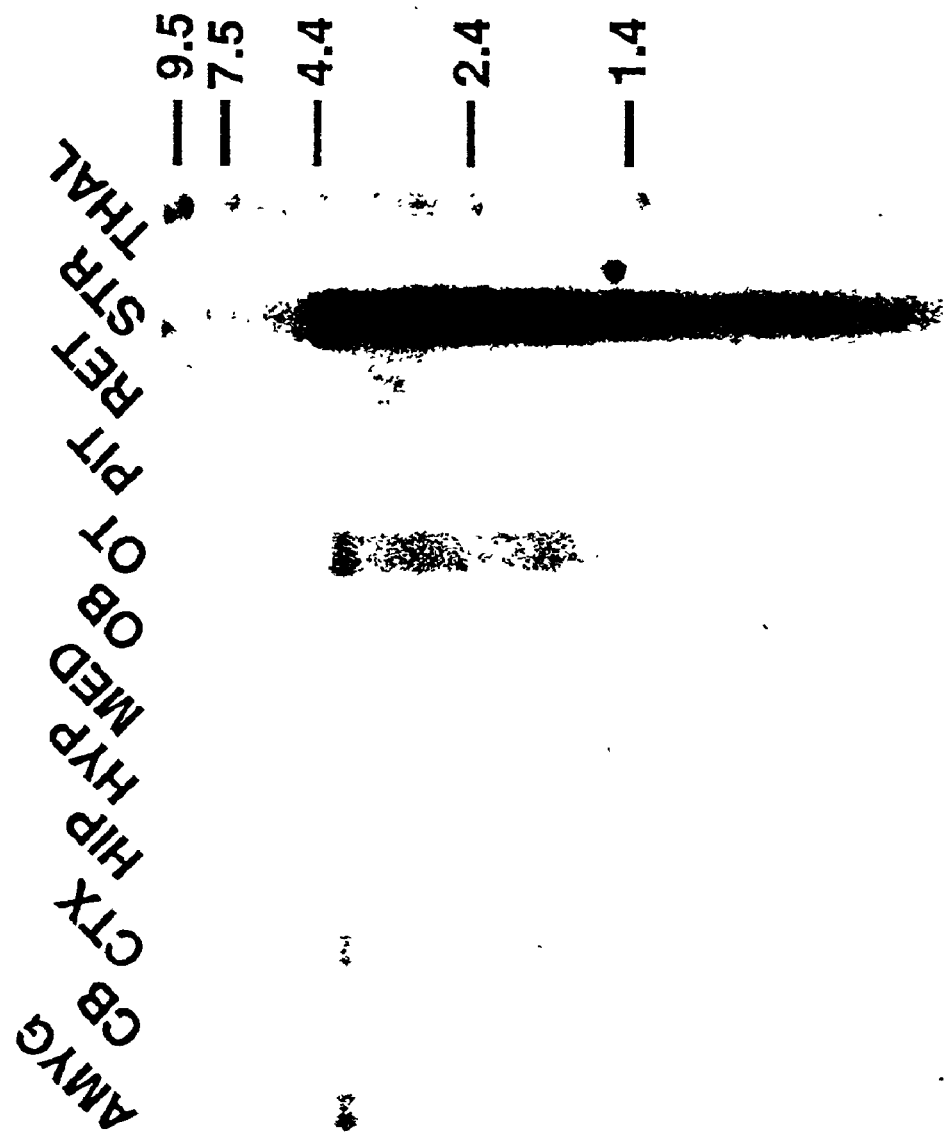
FIG. 3: Northern blot analysis of St-B17 RNA transcripts in rat brain. Each lane contained 3 μg of poly (A+) RNA. Lanes: AMYG, amygdala; CB, cerebellum; CTX, cerebral cortex; HIP, hippocampus; HYP, hypothalamus; MED, medulla; OB, olfactory bulb; OT, olfactory tubercle; PIT, pituitary; RET, retina; STR, striatum; THAL, thalamus. Locations of RNA size (kb) markers are indicated.

FIG. 3 shows a Northern blot analysis of St-B17 RNA transcripts in rat brain. Each lane contained 3 μg of poly (A+) RNA. Lanes: AMYG, amygdala; CB, cerebellum; CTX, cerebral cortex; HIP, hippocampus; HYP, hypothalamus; MED, medulla; OB, olfactory bulb; OT, olfactory tubercle; PIT, pituitary; RET, retina; STR, striatum; THAL, thalamus. Locations of RNA size (kb) markers are indicated.

To prepare the Northern blot, poly (A+) RNA was prepared from rat brain regions using the FASTTRACK© mRNA isolation system (INVITROGEN). 3 μg of poly (A+) RNA was denatured and subjected to electrophoresis on a 1% agarose gel containing 0.66 M formaldehyde. RNA was transferred to a nylon membrane (Genescreen Plus, Dupont) by capillary transfer and immobilized by UV crosslinking. Northern blots were probed with the entire 2.8 kb cDNA insert of clone St-B17 [$^{32}$P]-labeled by the random primer method. Northern blots were hybridized with 3×10$^6$ dpm/ml of probe in 1 M NaCl, 1% SDS, 10% dextran sulfate at 60° C. for 18 hr. Blots were washed in 2×SSC/1% SDS at room temperature, followed by 0.2×SSC/1% SDS at 65° C., and were exposed with an intensifying screen for 15 days at −70° C.

A single transcript of 4.2 kb was observed in various brain regions with highest expression appearing to occur in the corpus striatum (FIG. 3). St-B17 mRNA was also observed in the amygdala, cerebral cortex and olfactory tubercle whereas it was absent, or present in undetectable levels, in the cerebellum, hippocampus, hypothalamus, medulla, olfactory bulb, pituitary, retina and thalamus. Similarly, no transcript was observed, even after prolonged exposures, in Northern blots of mRNA from rat heart, lung, kidney, spleen, pancreas, smooth muscle, skeletal muscle, stomach, ovary, prostrate, or testes (data not shown).

This result indicates that the St-B17 receptor is produced in much higher levels in the corpus striatum than in other regions of the brain. In addition, the receptor is undetectable in non-brain tissues.

The localization of St-B17 mRNA to limbic and cortical regions, and the relatively potent interaction of several therapeutically important drugs, including the atypical anti-psychotic clozapine, the typical anti-psychotic loxapine, and the tricyclic anti-depressants amoxipine, clomiprimine, amitriptyline, and nortriptyline with St-B17 suggests that this receptor may play an important though hitherto unappreciated role in several neuropsychiatric disorders which involve serotonergic systems.

In addition to the mRNA distribution of St-B17, we were also interested in the intracellular cascade of events following agonist binding to the receptor. One possible mechanism of receptor signaling involved adenylate cyclase activity. To investigate this possibility, the following experiment was performed.

EXAMPLE 8

Analysis of Receptor Mediated cAMP Activity

Human Embryonic Kidney cells (HEK 293 available from the ATCC) were stably co-transfected in 150mm dishes by the CaPO$_4$ technique with 30 µg of pSRα-B17 and 3 µg of pMam-neo (INVITROGEN). These HEK 293 cells were then subjected to selection with 600 µg/ml genetecin (G418) (GIBCO). The resistant colonies were collected and screened for receptor expression by [$^{125}$I]-LSD binding as described in Example 6. One clone was isolated which expressed approximately 800 fMoles/mg St-B17 receptor protein and was subsequently used for assessment of cAMP accumulation.

Intracellular cAMP levels were determined after a 5 minute incubation of intact cells with various test compounds at 37° C. in the presence of the cAMP phosphodiesterase inhibitor RO-20-1724, using a modification of a previously described cAMP assay (Monsma, F. J., Jr., Barton, A. C., and Sibley, D. R. (1990) *J. Neurochemistry* 54, 1200–1207) wherein the adrenal cAMP binding protein was replaced with 0.8 mg/ml protein kinase A in water.

Figure 4:
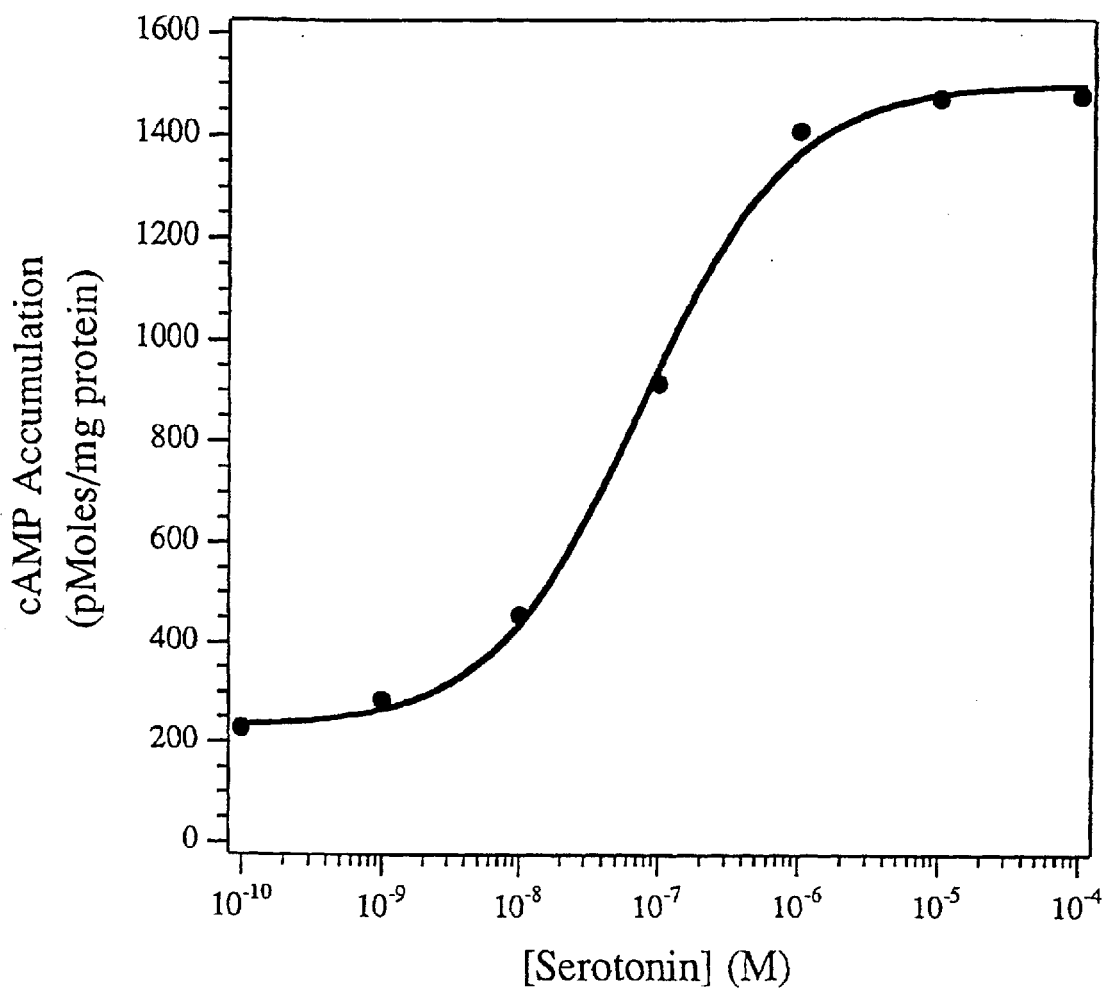
FIG. 4: Accumulation of cAMP in response to agonist activation of St-B17 stably expressed in HEK-293 cells. This figure shows a dose-response curve activation of St-B17 by serotonin in stably transfected, intact HEK-293 cells.

As shown in FIG. 4, serotonin causes a potent dose-dependent increase in cAMP levels in transfected HEK-293 cells with an average 50% effective concentration (EC$_{50}$) of 145 (±40, n=3) nM, whereas there was no detectable response in un-transfected cells (data not shown). This suggests that the St-B17 receptor mediates some part of its cell signaling through a cAMP-related pathway.

Figure 5:
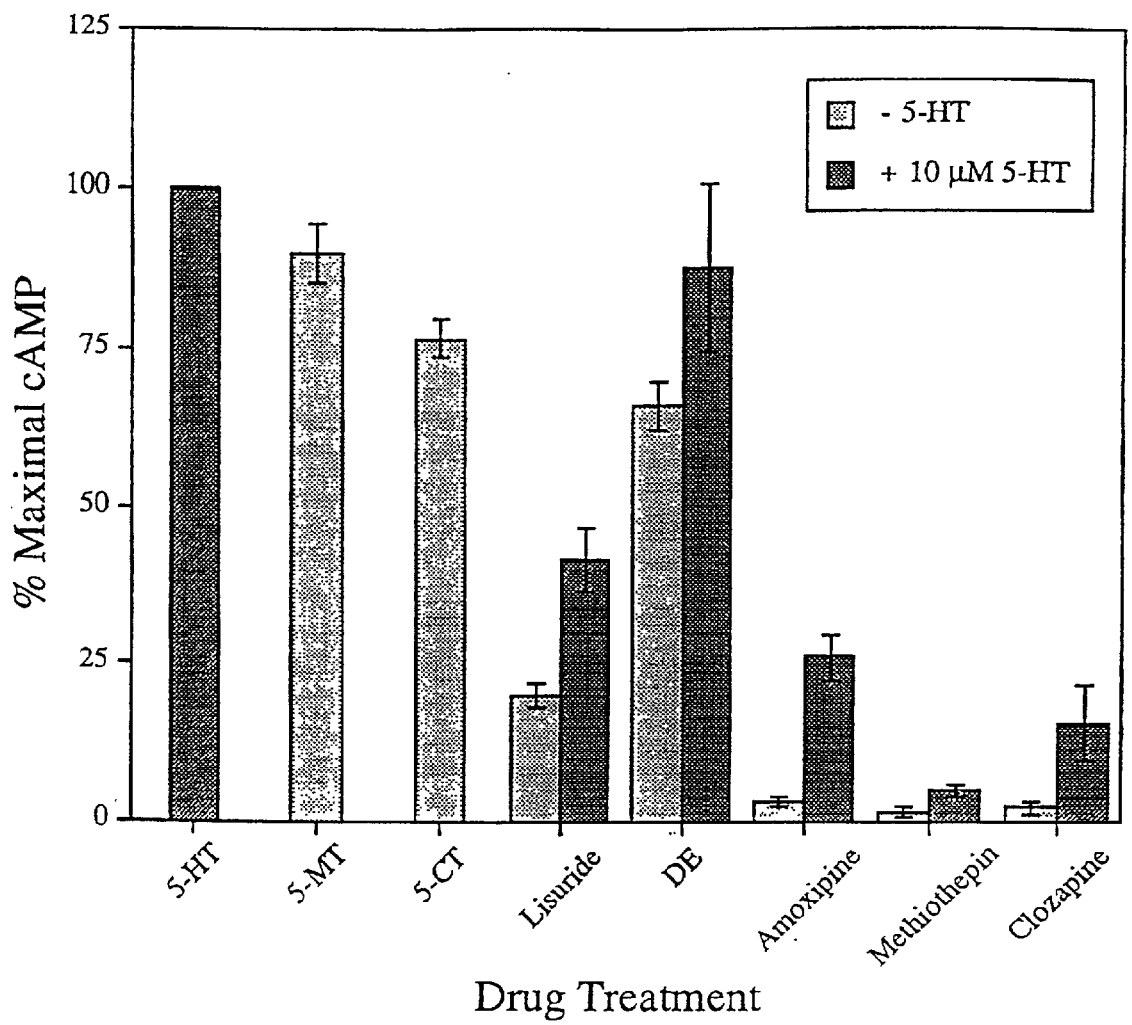
FIG. 5: Pharmacological analysis of serotonin stimulated cAMP accumulation in stably transfected HEK-293 cells. DE is an acronym for dihydroergocryptine. All drugs were assayed at 10 μM final concentration.

A pharmacological analysis of the cAMP response (FIG. 5) indicates that the serotonergic agonists 5-MT and 5-CT are also able to elicit an increase in cAMP levels. The ergot alkaloids lisuride and dihydroergotamine also stimulate cAMP accumulation, although these drugs appear to function as partial agonists to the St-B17 receptor. Amoxipine, methiothepin and clozapine (FIG. 5) all appear to act as antagonists of this receptor as they had no significant effect on cAMP levels on their own, but were able to substantially inhibit the response elicited by 5-HT. These data suggest that the St-B17 receptor is functionally linked to the adenylyl cyclase signal transduction system.

The measurement of cAMP levels in a cell transfected with St-B17 can thereby provide an assay for detecting potential agonists and antagonists of serotonin receptors. Using the above method, we can analyze the accumulated level of cAMP in the cell after treatment with a drug to be tested. A lowering of the cAMP level in the presence of 5-HT indicates a drug which has inhibitory affects on 5-HT receptor binding.

We were also interested in isolating the human variation of the present invention. Our method of isolating the human receptor is discussed below.

EXAMPLE 9

Isolation of the Human St-B17 Receptor

Two different restriction fragments derived from the rat St-B17 gene were used as probes to retrieve the human homolog. A 1192 base-pair Xma I-BstXI fragment and a 655 base-pair Bam HI-EagI fragment of rat St-B17 were labeled with [α$^{32}$P]-dCTP using the well known nick-translation method. These labeled fragments were then used to screen a commercially available human genomic library (Stratagene #946205).

The library was plated onto host cells C600 and PLK17 respectively, and duplicate nylon (Nytran, Schleicher and Schuell) lifts made. Each of the labeled fragments was hybridized (6×SSC at 55° C., pH7) and washed (2×SSC, 58° C.) at moderate stringency. Positive isolates were plaque purified through a second round of hybridization.

An insert from each positive plaque isolate was excised by EcoRI digestion, and then subcloned into a corresponding site in the phagemid vector pBluescript SK(−) (Stratagene). These inserts were then digested with several restriction enzymes, and run on a Southern Blot. Fragments hybridizing to labeled St-B17 rat sequences were identified by Southern hybridization. Hybridizing fragments were then subcloned into pBluescript SK(−) as discussed above. The nucleic acid sequence of these inserts was then determined by dideoxynucleotide termination using Sequenase (United States Biochemicals) in conjunction with standard subcloning techniques. The nucleotide sequence of the human St-B17 gene is SEQUENCE ID NO:12. The corresponding amino acid sequence is SEQUENCE ID NO: 13.

It should be understood that all of the previous experiments relating to identification of binding ligands to the rat receptor can be performed in a similar fashion with the human gene. For instance, the human gene can be cloned into an expression plasmid and placed in COS-7 cells by methods similar to those discussed above, and used to assay binding of competitors such as those revealed in Table 1. This would provide a method of assaying inhibitors of serotonin binding to the St-B17 receptor.

Specifically, Example 8 can be repeated with the human receptor to reveal if a particular compound was mimicking or inhibiting the binding of serotonin by measurement of the relative level of cAMP before and after treatment with the compound. The methods of this example can also be repeated with cDNA of other mammals or other vertebrates to obtain the corresponding St-B17 receptor from these organisms.

Other experiments are also contemplated relating to discovering which cells in vivo express the receptor gene on their surface. To allow us the ability to study the expression of the receptor on cell surfaces throughout the body, we needed to produce antibodies against the receptor protein. A method for producing antibodies is discussed below in Example 10.

EXAMPLE 10

Production of Antibodies Against St-B17

COS-7 cells expressing the St-B17 receptor protein derived in Examples 11 and 12 are lysed with NP40, and the isolated membranes are injected into rabbits. The lysed membranes are isolated in a non-ionic detergent so as not to affect the membrane bound receptors. Freunds adjuvant is used in the injection to help stimulate an antigenic response by the rabbits. After two booster shots of the lysed membranes, the rabbits are bled and the sera isolated by centrifugation.

The antibodies in the crude rabbit sera extract are $^{125}$I labeled by well known methods, and tested for activity against the transfected COS-7 cells. A western blot having one lane containing proteins from transfected cell lysates, and a second lane having untransfected lysates (control) is run. A strong band indicating antibody binding at 46.8 kd in the transfected cell lane, that is not apparent in the untransfected lane shows that polyclonal antibodies against the St-B17 receptor protein have been properly isolated.

Monoclonal antibodies can be made by well known methods in addition to the polyclonal antibodies discussed above. One method of producing monoclonal antibodies is discussed below in Example 11.

EXAMPLE 11

Production of Monoclonal Antibodies Against St-B17

The St-B17 transfected COS-7 cells produced in the previous examples are lysed with NP-40 and the cell membranes are pelleted by centrifugation. The isolated membranes, having bound St-B17 receptor proteins are injected in Freunds adjuvant into mice. After being injected 9 times over a three week period, the mice spleens are removed and resuspended in PBS.

The suspended spleen cells are mixed (approximately 4:1 with SP 2/0 Myeloma cells. Polyethylene glycol is added to fuse the myeloma cells to the spleen cells, and the fused cells are selected in HAT media. The fused cells are aliquoted so that only one cell is grown in each well of a 96 well microtiter plate. Each cell is grown and the media removed and secreted proteins are $^{125}$I labeled. The labeled media from each well is used to probe a Western blot of transfected and untransfected COS-7 cells (see Example 12). The desired fusion cell will produce a monoclonal antibody that strongly binds a 46.8 kD band in the transfected COS-7 cell lane on the Western blot, but doesn't bind to any other protein in that lane, or the control lane.

This method provides a way of detecting expression of the St-B17 serotonin receptor protein. Another method of detecting expression of St-B17 is by in situ hybridization as discussed below in Example 12.

EXAMPLE 12

In Situ Hybridization of St-B17

In situ hybridization allows the identification of mRNA within intact tissues, such as the rat brain. In this method, oligonucleotides corresponding to unique portions of the St-B17 gene (SEQ ID NO: 7) are used to detect specific mRNA species in the brain.

An anesthetized rat is transcardially perfused with cold PBS (5–20 minutes), followed by perfusion with a 4% formaldehyde solution. The brain is removed, frozen in liquid nitrogen, and cut into 5 µm to 30 µm sections. The sections are placed on slides and incubated in proteinase K for approximately 15 minutes. The slides are then rinsed in DEP, water, and ethanol, and placed in a prehybridization buffer.

A radioactive probe corresponding to primer P1 is made by nick translation and incubated with the sectioned brain tissue. After incubation and air drying, the labeled areas are visualized by autoradiography. Dark spots on the tissue sample indicate hybridization of the probe with the brain mRNA thereby demonstrating expression of the St-B17 receptor.

All of the above cited references are herein incorporated by reference. The present invention should not be limited by these examples but only by the following claims.

What is claimed is:

1. An isolated nucleotide secquence encoding a serotonin receptor protein 5-HT$_6$, said nucleotide sequence being selected from:
   (a) a nucleotide sequence comprising SEQ ID NO:7;
   (b) a nucleotide sequence comprising SEQ ID NO:12;
   (c) a nucleotide sequence from a human genomic library hybridizing under moderate stringency conditions at 6×SSC and 55° C., pH7, to a 1192 bp XmaI-BstXI and a 655 bp BamHI-EagI fragment from SEQ ID NO:7; or
   (d) a nucleotide sequence encoding a protein having the amino acid sequence shown by SEQ ID NO:8 or SEQ ID NO: 13.

2. The nucleotide sequence according to claim 1, wherein said nucleotide sequence is selected from (a).

3. The nucleotide sequence according to claim 1, wherein said nucleotide sequence is selected from (b).

4. The nucleotide sequence according to claim 1, wherein said nucleotide sequence is selected from (c).

5. The nucleotide sequence according to claim 1, wherein said nucleotide sequence is selected from (d).

6. A recombinant construct comprising the nucleotide sequence according to claim 1, operably linked to a heterologous propoter.

7. The recombinant construct according to claim 6, which is an expression vector.

8. The recombinant construct according to claim 7, which is a eukaryotic expression vector.

9. A mammalian cell line comprising the nude tide sequence of claim 1, said mammalian cell line expressing 5-HT$_6$ serotonin receptor.

10. The cell line of claim 9, wherein said cells are derived from a human.

11. The cell line of claim 10, wherein said cells are HEK 293.

12. An isolated protein encoded by the nucleotide sequence of any of claims 1–5.

* * * * *

UNITED STATES PATENT AND TRADEMARK OFFICE
CERTIFICATE OF CORRECTION

PATENT NO. : 6,844,190 B2
DATED : January 18, 2005
INVENTOR(S) : Sibley et al.

It is certified that error appears in the above-identified patent and that said Letters Patent is hereby corrected as shown below:

Title page,
Item [73], Assignee, delete "The United States of America as represented by the Department of Health and Human Services" and insert -- The Government of the United States of America, as represented by the Secretary, Department of Health and Human Services --.

Column 35,
Line 51, delete "secquence" and insert -- sequence --.
Line 55, after "sequence" and before "from a human genomic library" insert -- obtainable --.
Line 58, delete "6xSSC" and insert -- 6XSSC --.

Column 36,
Line 54, delete "propoter" and insert -- promoter --.
Line 58, delete "nude tide" and insert -- nucleotide --.

Signed and Sealed this

Twentieth Day of December, 2005

JON W. DUDAS
*Director of the United States Patent and Trademark Office*

SEQUENCE LISTING

<160> NUMBER OF SEQ ID NOS: 13

<210> SEQ ID NO 1
<211> LENGTH: 33
<212> TYPE: DNA
<213> ORGANISM: Artificial Sequence
<220> FEATURE:
<223> OTHER INFORMATION: primer

<400> SEQUENCE: 1
gtcgaccctk tksgccmtca kcayrgrtcg cta                33

<210> SEQ ID NO 2
<211> LENGTH: 35
<212> TYPE: DNA
<213> ORGANISM: Artificial Sequence
<220> FEATURE:
<223> OTHER INFORMATION: primer

<400> SEQUENCE: 2
aagcttatga araagggcag scarcagagg kyrma              35

<210> SEQ ID NO 3
<211> LENGTH: 33
<212> TYPE: DNA
<213> ORGANISM: Artificial Sequence
<220> FEATURE:
<223> OTHER INFORMATION: primer -continued

```
<400> SEQUENCE: 3
aagcatagca ggaaggcctt gaaggccagc ctg                                    33

<210> SEQ ID NO 4
<211> LENGTH: 33
<212> TYPE: DNA
<213> ORGANISM: Artificial Sequence
<220> FEATURE:
<223> OTHER INFORMATION: primer

<400> SEQUENCE: 4
ggcgagaaat acgccctgaa gttctcccgg gac                                    33

<210> SEQ ID NO 5
<211> LENGTH: 30
<212> TYPE: DNA
<213> ORGANISM: Artificial Sequence
<220> FEATURE:
<223> OTHER INFORMATION: primer

<400> SEQUENCE: 5
ttgccaatac tactctaagg tgcagcttcc                                        30

<210> SEQ ID NO 6
<211> LENGTH: 30
<212> TYPE: DNA
<213> ORGANISM: Artificial Sequence
<220> FEATURE:
<223> OTHER INFORMATION: primer

<400> SEQUENCE: 6
cacacgactt aactccatag agtcgatcgg                                        30

<210> SEQ ID NO 7
<211> LENGTH: 1914
<212> TYPE: DNA
<213> ORGANISM: Rat
<220> FEATURE:
<221> NAME/KEY: CDS
<222> LOCATION: (439)...(1749)

<400> SEQUENCE: 7
ccaaccccca cgcgcgacac gtggtgatct aacgtactca cacgcccacc cttctcgaag        60
agactgcccc ggccggaagg cgggagttcg gctcctgctc ccacatcccc agctgtgccc       120
ctagccagga accccacccc catcttatgg catcccggt  ggccctattc catcccaggg       180
ctctcatcca gccccaagct aactttcatt gactcgtcac atcagtaccc ctccccaaac       240
ttcttacccg agtactccag gtggccctgc gtaggaggca cccctacaac tcctcccgat       300
ctcttgaaat cgctgctcga tgacctaaga accccgtttt gccaatacta ctctaaggtg       360
cagcttcctt tctcctcctt tgccttcacc ctgtacctgc agtcaccata tcccgtcttg       420
gtcctcaacc cagtcccc atg gtt cca gag cca ggc cct gtc aac agt agc        471
                    Met Val Pro Glu Pro Gly Pro Val Asn Ser Ser
                      1               5                  10 acc cca gcc tgg ggt ccc ggg cca ccg cct gct ccg ggg ggc agc ggc        519
Thr Pro Ala Trp Gly Pro Gly Pro Pro Pro Ala Pro Gly Gly Ser Gly
             15                  20                  25 tgg gtg gct gcc gcg ctg tgc gtg gtc atc gtg ctg aca gca gcc gcc        567
Trp Val Ala Ala Ala Leu Cys Val Val Ile Val Leu Thr Ala Ala Ala
         30                  35                  40 aat tcg ctg ctg atc gtg ctc att tgc acg cag ccc gcc gtg cgc aac        615
Asn Ser Leu Leu Ile Val Leu Ile Cys Thr Gln Pro Ala Val Arg Asn
```

```
                     45                  50                  55
acg tct aac ttc ttt ctg gtg tcg ctc ttc acg tcg gac ttg atg gtg      663
Thr Ser Asn Phe Phe Leu Val Ser Leu Phe Thr Ser Asp Leu Met Val
 60                  65                  70                  75 ggg ttg gtg gtg atg ccc cca gcc atg ctg aac gcg ctg tat ggg cgc      711
Gly Leu Val Val Met Pro Pro Ala Met Leu Asn Ala Leu Tyr Gly Arg
                 80                  85                  90 tgg gtg tta gct cga ggc ctc tgt ctg ctt tgg act gcc ttc gac gtg      759
Trp Val Leu Ala Arg Gly Leu Cys Leu Leu Trp Thr Ala Phe Asp Val
             95                 100                 105 atg tgc tgc agc gcc tcc atc ctc aac ctc tgc ctc atc agc ctg gac      807
Met Cys Cys Ser Ala Ser Ile Leu Asn Leu Cys Leu Ile Ser Leu Asp
        110                 115                 120 cgc tac ctg ctc atc ctc tcg ccg ctg cgc tac aag ctg cgc atg aca      855
Arg Tyr Leu Leu Ile Leu Ser Pro Leu Arg Tyr Lys Leu Arg Met Thr
    125                 130                 135 gcc ccg cga gcc ctg gcg ctc atc ctg ggt gcc tgg agc ctc gcg gcg      903
Ala Pro Arg Ala Leu Ala Leu Ile Leu Gly Ala Trp Ser Leu Ala Ala
140                 145                 150                 155 ctt gcc tcc ttc cta ccc ctc ttg ctg ggc tgg cac gaa ctg ggc aaa      951
Leu Ala Ser Phe Leu Pro Leu Leu Leu Gly Trp His Glu Leu Gly Lys
                160                 165                 170 gct cga aca cct gcc cct ggc cag tgc cgc cta ttg gcc agc ctg cct      999
Ala Arg Thr Pro Ala Pro Gly Gln Cys Arg Leu Leu Ala Ser Leu Pro
            175                 180                 185 ttt gtc ctc gtg gcg tcc ggc gtc acc ttt ttc ctg cct tcg ggt gcc     1047
Phe Val Leu Val Ala Ser Gly Val Thr Phe Phe Leu Pro Ser Gly Ala
        190                 195                 200 atc tgc ttc acc tac tgc agg atc ctt ctg gct gcc cgc aag cag gcg     1095
Ile Cys Phe Thr Tyr Cys Arg Ile Leu Leu Ala Ala Arg Lys Gln Ala
    205                 210                 215 gtg caa gtg gcc tcg ctc acc acg ggc acg gct ggc cag gcc ttg gaa     1143
Val Gln Val Ala Ser Leu Thr Thr Gly Thr Ala Gly Gln Ala Leu Glu
220                 225                 230                 235 acc ttg cag gtg ccc agg aca cca cgc cca ggg atg gag tcc gct gac     1191
Thr Leu Gln Val Pro Arg Thr Pro Arg Pro Gly Met Glu Ser Ala Asp
                240                 245                 250 agt agg cgt ctg gcc acc aag cat agc agg aag gcc ttg aag gcc agc     1239
Ser Arg Arg Leu Ala Thr Lys His Ser Arg Lys Ala Leu Lys Ala Ser
            255                 260                 265 ctg acc ctg ggc atc ctg ctg gga atg ttc ttt gtc acc tgg ctg ccc     1287
Leu Thr Leu Gly Ile Leu Leu Gly Met Phe Phe Val Thr Trp Leu Pro
        270                 275                 280 ttc ttt gtg gcc aac ata gct cag gcc gtg tgt gac tgc atc tcc cca     1335
Phe Phe Val Ala Asn Ile Ala Gln Ala Val Cys Asp Cys Ile Ser Pro
    285                 290                 295 ggc ctc ttc gat gtc ctc aca tgg ctg ggg tac tgt aat agc acc atg     1383
Gly Leu Phe Asp Val Leu Thr Trp Leu Gly Tyr Cys Asn Ser Thr Met
300                 305                 310                 315 aac cct atc atc tac ccg ctc ttt atg cgg gac ttc aag agg gcc ctg     1431
Asn Pro Ile Ile Tyr Pro Leu Phe Met Arg Asp Phe Lys Arg Ala Leu
                320                 325                 330 ggc agg ttc ctg cat gcg tcc act gtc ccc cgg agc acc ggc cag ccc     1479
Gly Arg Phe Leu His Ala Ser Thr Val Pro Arg Ser Thr Gly Gln Pro
            335                 340                 345 tgc ctc ccc ctc cat gtg gac ctc tca cag cgg tgc cag acc agg cct     1527
Cys Leu Pro Leu His Val Asp Leu Ser Gln Arg Cys Gln Thr Arg Pro
        350                 355                 360 cag ctg cag cag gtg ctc gct ctg cct ctg ccg cca aac tca gat tca     1575
```

-continued

```
Gln Leu Gln Gln Val Leu Ala Leu Pro Leu Pro Pro Asn Ser Asp Ser
    365                 370                 375 gac tcc gct tca ggg ggc acc tcg ggc ctg cag ctc aca gcc cag ctt    1623
Asp Ser Ala Ser Gly Gly Thr Ser Gly Leu Gln Leu Thr Ala Gln Leu
380                 385                 390                 395 ctg ctg cct gga gag gcc aca cgg gac ccc ccg cca ccc acc agg gcc    1671
Leu Leu Pro Gly Glu Ala Thr Arg Asp Pro Pro Pro Pro Thr Arg Ala
                400                 405                 410 acc act gtg gtc aac ttc ttt gtc aca gac tct gtg gag cct gag ata    1719
Thr Thr Val Val Asn Phe Phe Val Thr Asp Ser Val Glu Pro Glu Ile
            415                 420                 425 cgg ccg cat cca ctc agt tcc ccc gtg aac tgaccaggtc aagagctggc      1769
Arg Pro His Pro Leu Ser Ser Pro Val Asn
        430                 435 cattggaggc cacattcccg gagctctcag cccactctcc ctgagactag gaggtggtag  1829
gtctcctgag agtgtgctga attgaggtat ctcagctagc ccatcttctg ctgcagctcc  1889
ttgactgagg ggtagtcaga cacat                                        1914
```

<210> SEQ ID NO 8
<211> LENGTH: 437
<212> TYPE: PRT
<213> ORGANISM: Rat

<400> SEQUENCE: 8

```
Met Val Pro Glu Pro Gly Pro Val Asn Ser Ser Thr Pro Ala Trp Gly
1               5                   10                  15

Pro Gly Pro Pro Pro Ala Pro Gly Gly Ser Gly Trp Val Ala Ala Ala
            20                  25                  30

Leu Cys Val Val Ile Val Leu Thr Ala Ala Ala Asn Ser Leu Leu Ile
        35                  40                  45

Val Leu Ile Cys Thr Gln Pro Ala Val Arg Asn Thr Ser Asn Phe Phe
    50                  55                  60

Leu Val Ser Leu Phe Thr Ser Asp Leu Met Val Gly Leu Val Val Met
65                  70                  75                  80

Pro Pro Ala Met Leu Asn Ala Leu Tyr Gly Arg Trp Val Leu Ala Arg
                85                  90                  95

Gly Leu Cys Leu Leu Trp Thr Ala Phe Asp Val Met Cys Cys Ser Ala
            100                 105                 110

Ser Ile Leu Asn Leu Cys Leu Ile Ser Leu Asp Arg Tyr Leu Leu Ile
        115                 120                 125

Leu Ser Pro Leu Arg Tyr Lys Leu Arg Met Thr Ala Pro Arg Ala Leu
    130                 135                 140

Ala Leu Ile Leu Gly Ala Trp Ser Leu Ala Ala Leu Ala Ser Phe Leu
145                 150                 155                 160

Pro Leu Leu Leu Gly Trp His Glu Leu Gly Lys Ala Arg Thr Pro Ala
                165                 170                 175

Pro Gly Gln Cys Arg Leu Leu Ala Ser Leu Pro Phe Val Leu Val Ala
            180                 185                 190

Ser Gly Val Thr Phe Phe Leu Pro Ser Gly Ala Ile Cys Phe Thr Tyr
        195                 200                 205

Cys Arg Ile Leu Leu Ala Ala Arg Lys Gln Ala Val Gln Val Ala Ser
    210                 215                 220

Leu Thr Thr Gly Thr Ala Gly Gln Ala Leu Glu Thr Leu Gln Val Pro
225                 230                 235                 240

Arg Thr Pro Arg Pro Gly Met Glu Ser Ala Asp Ser Arg Arg Leu Ala
```

```
                245                 250                 255
Thr Lys His Ser Arg Lys Ala Leu Lys Ala Ser Leu Thr Leu Gly Ile
            260                 265                 270

Leu Leu Gly Met Phe Phe Val Thr Trp Leu Pro Phe Phe Val Ala Asn
        275                 280                 285

Ile Ala Gln Ala Val Cys Asp Cys Ile Ser Pro Gly Leu Phe Asp Val
        290                 295                 300

Leu Thr Trp Leu Gly Tyr Cys Asn Ser Thr Met Asn Pro Ile Ile Tyr
305                 310                 315                 320

Pro Leu Phe Met Arg Asp Phe Lys Arg Ala Leu Gly Arg Phe Leu His
                325                 330                 335

Ala Ser Thr Val Pro Arg Ser Thr Gly Gln Pro Cys Leu Pro Leu His
            340                 345                 350

Val Asp Leu Ser Gln Arg Cys Gln Thr Arg Pro Gln Leu Gln Gln Val
        355                 360                 365

Leu Ala Leu Pro Leu Pro Pro Asn Ser Asp Ser Asp Ser Ala Ser Gly
370                 375                 380

Gly Thr Ser Gly Leu Gln Leu Thr Ala Gln Leu Leu Pro Gly Glu
385                 390                 395                 400

Ala Thr Arg Asp Pro Pro Pro Thr Arg Ala Thr Thr Val Val Asn
                405                 410                 415

Phe Phe Val Thr Asp Ser Val Glu Pro Glu Ile Arg Pro His Pro Leu
            420                 425                 430

Ser Ser Pro Val Asn
        435

<210> SEQ ID NO 9
<211> LENGTH: 2108
<212> TYPE: DNA
<213> ORGANISM: Rat
<220> FEATURE:
<221> NAME/KEY: CDS
<222> LOCATION: (439)...(1311)
<221> NAME/KEY: intron
<222> LOCATION: (1312)...(1505)
<221> NAME/KEY: CDS
<222> LOCATION: (1506)...(1943)

<400> SEQUENCE: 9
ccaaccccca cgcgcgacac gtggtgatct aacgtactca cacgcccacc cttctcgaag      60
agactgcccc ggccggaagg cgggagttcg gctcctgctc ccacatcccc agctgtgccc    120
ctagccagga accccacccc catcttatgg catccccggt ggccctattc catcccaggg    180
ctctcatcca gccccaagct aactttcatt gactcgtcac atcagtaccc ctccccaaac    240
ttcttacccg agtactccag gtggccctgc gtaggaggca cccctacaac tcctcccgat    300
ctcttgaaat cgctgctcga tgacctaaga accccgtttt gccaatacta ctctaaggtg    360
cagcttcctt tctcctcctt tgccttcacc ctgtacctgc agtcaccata tcccgtcttg    420
gtcctcaacc cagtcccc atg gtt cca gag cca ggc cct gtc aac agt agc     471
                    Met Val Pro Glu Pro Gly Pro Val Asn Ser Ser
                      1               5                  10 acc cca gcc tgg ggt ccc ggg cca ccg cct gct ccg ggg ggc agc ggc     519
Thr Pro Ala Trp Gly Pro Gly Pro Pro Pro Ala Pro Gly Gly Ser Gly
            15                  20                  25 tgg gtg gct gcc gcg ctg tgc gtg gtc atc gtg ctg aca gca gcc gcc    567
Trp Val Ala Ala Ala Leu Cys Val Val Ile Val Leu Thr Ala Ala Ala
        30                  35                  40
```

-continued

| | |
|---|---|
| aat tcg ctg ctg atc gtg ctc att tgc acg cag ccc gcc gtg cgc aac<br>Asn Ser Leu Leu Ile Val Leu Ile Cys Thr Gln Pro Ala Val Arg Asn<br>      45                    50                  55 | 615 |
| acg tct aac ttc ttt ctg gtg tcg ctc ttc acg tcg gac ttg atg gtg<br>Thr Ser Asn Phe Phe Leu Val Ser Leu Phe Thr Ser Asp Leu Met Val<br>60                    65                    70                    75 | 663 |
| ggg ttg gtg gtg atg ccc cca gcc atg ctg aac gcg ctg tat ggg cgc<br>Gly Leu Val Val Met Pro Pro Ala Met Leu Asn Ala Leu Tyr Gly Arg<br>                  80                    85                  90 | 711 |
| tgg gtg tta gct cga ggc ctc tgt ctg ctt tgg act gcc ttc gac gtg<br>Trp Val Leu Ala Arg Gly Leu Cys Leu Leu Trp Thr Ala Phe Asp Val<br>                  95                  100               105 | 759 |
| atg tgc tgc agc gcc tcc atc ctc aac ctc tgc ctc atc agc ctg gac<br>Met Cys Cys Ser Ala Ser Ile Leu Asn Leu Cys Leu Ile Ser Leu Asp<br>110                    115                  120 | 807 |
| cgc tac ctg ctc atc ctc tcg ccg ctg cgc tac aag ctg cgc atg aca<br>Arg Tyr Leu Leu Ile Leu Ser Pro Leu Arg Tyr Lys Leu Arg Met Thr<br>125                    130                  135 | 855 |
| gcc ccg cga gcc ctg gcg ctc atc ctg ggt gcc tgg agc ctc gcg gcg<br>Ala Pro Arg Ala Leu Ala Leu Ile Leu Gly Ala Trp Ser Leu Ala Ala<br>140                145                150               155 | 903 |
| ctt gcc tcc ttc cta ccc ctc ttg ctg ggc tgg cac gaa ctg ggc aaa<br>Leu Ala Ser Phe Leu Pro Leu Leu Leu Gly Trp His Glu Leu Gly Lys<br>                  160                  165               170 | 951 |
| gct cga aca cct gcc cct ggc cag tgc cgc cta ttg gcc agc ctg cct<br>Ala Arg Thr Pro Ala Pro Gly Gln Cys Arg Leu Leu Ala Ser Leu Pro<br>                  175                  180               185 | 999 |
| ttt gtc ctc gtg gcg tcc ggc gtc acc ttt ttc ctg cct tcg ggt gcc<br>Phe Val Leu Val Ala Ser Gly Val Thr Phe Phe Leu Pro Ser Gly Ala<br>                  190                  195               200 | 1047 |
| atc tgc ttc acc tac tgc agg atc ctt ctg gct gcc cgc aag cag gcg<br>Ile Cys Phe Thr Tyr Cys Arg Ile Leu Leu Ala Ala Arg Lys Gln Ala<br>                  205                  210               215 | 1095 |
| gtg caa gtg gcc tcg ctc acc acg ggc acg gct ggc cag gcc ttg gaa<br>Val Gln Val Ala Ser Leu Thr Thr Gly Thr Ala Gly Gln Ala Leu Glu<br>220                    225                  230               235 | 1143 |
| acc ttg cag gtg ccc agg aca cca cgc cca ggg atg gag tcc gct gac<br>Thr Leu Gln Val Pro Arg Thr Pro Arg Pro Gly Met Glu Ser Ala Asp<br>                  240                  245               250 | 1191 |
| agt agg cgt ctg gcc acc aag cat agc agg aag gcc ttg aag gcc agc<br>Ser Arg Arg Leu Ala Thr Lys His Ser Arg Lys Ala Leu Lys Ala Ser<br>                  255                  260               265 | 1239 |
| ctg acc ctg gga atc ctg ctg gga atg ttc ttt gtc acc tgg ctg ccc<br>Leu Thr Leu Gly Ile Leu Leu Gly Met Phe Phe Val Thr Trp Leu Pro<br>                  270                  275               280 | 1287 |
| ttc ttt gtg gcc aac ata gct cag gtaaaatgat gaccgtgaag gtgggatgag<br>Phe Phe Val Ala Asn Ile Ala Gln<br>285                    290 | 1341 |
| cttaggtctg accggagaga cgccatgctt cactgggcaa aggtgggagg gaggaggatg | 1401 |
| gctcatctgt ggtgcctgtg tctgtgtttc tgtcctatcc ctgctgggtg ggtagcctgg | 1461 |
| gtccctgcct gggacatggg gtgtgatgag tcttatctcc acag gcc gtg tgt gac<br>                                                                     Ala Val Cys Asp<br>                                                                         295 | 1517 |
| tgc atc tcc cca ggc ctc ttc gat gtc ctc aca tgg ctg ggg tac tgt<br>Cys Ile Ser Pro Gly Leu Phe Asp Val Leu Thr Trp Leu Gly Tyr Cys<br>                  300                  305               310 | 1565 |
| aat agc acc atg aac cct atc atc tac ccg ctc ttt atg cgg gac ttc<br>Asn Ser Thr Met Asn Pro Ile Ile Tyr Pro Leu Phe Met Arg Asp Phe<br>315                    320                  325 | 1613 |

```
aag agg gcc ctg ggc agg ttc ctg cat gcg tcc act gtc ccc cgg agc    1661
Lys Arg Ala Leu Gly Arg Phe Leu His Ala Ser Thr Val Pro Arg Ser
    330                 335                 340 acc ggc cag ccc tgc ctc ccc ctc cat gtg gac ctc tca cag cgg tgc    1709
Thr Gly Gln Pro Cys Leu Pro Leu His Val Asp Leu Ser Gln Arg Cys
345                 350                 355 cag acc agg cct cag ctg cag cag gtg ctc gct ctg cct ctg ccg cca    1757
Gln Thr Arg Pro Gln Leu Gln Gln Val Leu Ala Leu Pro Leu Pro Pro
360                 365                 370                 375 aac tca gat tca gac tcc gct tca ggg ggc acc tcg ggc ctg cag ctc    1805
Asn Ser Asp Ser Asp Ser Ala Ser Gly Gly Thr Ser Gly Leu Gln Leu
                380                 385                 390 aca gcc cag ctt ctg ctg cct gga gag gcc aca cgg gac ccc ccg cca    1853
Thr Ala Gln Leu Leu Leu Pro Gly Glu Ala Thr Arg Asp Pro Pro Pro
            395                 400                 405 ccc acc agg gcc acc act gtg gtc aac ttc ttt gtc aca gac tct gtg    1901
Pro Thr Arg Ala Thr Thr Val Val Asn Phe Phe Val Thr Asp Ser Val
        410                 415                 420 gag cct gag ata cgg ccg cat cca ctc agt tcc ccc gtg aac               1943
Glu Pro Glu Ile Arg Pro His Pro Leu Ser Ser Pro Val Asn
    425                 430                 435 tgaccaggtc aagagctggc cattggaggc cacattcccg agctctcag cccactctcc     2003 ctgagactag gaggtggtag gtctcctgag agtgtgctga attgaggtat ctcagctagc    2063
ccatcttctg ctgcagctcc ttgactgagg ggtagtcaga cacat                    2108

<210> SEQ ID NO 10
<211> LENGTH: 291
<212> TYPE: PRT
<213> ORGANISM: Rat

<400> SEQUENCE: 10

Met Val Pro Glu Pro Gly Pro Val Asn Ser Thr Pro Ala Trp Gly
1               5                   10                  15

Pro Gly Pro Pro Pro Ala Pro Gly Gly Ser Gly Trp Val Ala Ala
                20                  25                  30

Leu Cys Val Val Ile Val Leu Thr Ala Ala Ala Asn Ser Leu Leu Ile
            35                  40                  45

Val Leu Ile Cys Thr Gln Pro Ala Val Arg Asn Thr Ser Asn Phe Phe
50                  55                  60

Leu Val Ser Leu Phe Thr Ser Asp Leu Met Val Gly Leu Val Val Met
65                  70                  75                  80

Pro Pro Ala Met Leu Asn Ala Leu Tyr Gly Arg Trp Val Leu Ala Arg
                85                  90                  95

Gly Leu Cys Leu Leu Trp Thr Ala Phe Asp Val Met Cys Cys Ser Ala
            100                 105                 110

Ser Ile Leu Asn Leu Cys Leu Ile Ser Leu Asp Arg Tyr Leu Leu Ile
        115                 120                 125

Leu Ser Pro Leu Arg Tyr Lys Leu Arg Met Thr Ala Pro Arg Ala Leu
    130                 135                 140

Ala Leu Ile Leu Gly Ala Trp Ser Leu Ala Ala Leu Ala Ser Phe Leu
145                 150                 155                 160

Pro Leu Leu Leu Gly Trp His Glu Leu Gly Lys Ala Arg Thr Pro Ala
                165                 170                 175

Pro Gly Gln Cys Arg Leu Leu Ala Ser Leu Pro Phe Val Leu Val Ala
            180                 185                 190
```

Ser Gly Val Thr Phe Phe Leu Pro Ser Gly Ala Ile Cys Phe Thr Tyr
            195                 200                 205

Cys Arg Ile Leu Leu Ala Ala Arg Lys Gln Ala Val Gln Val Ala Ser
        210                 215                 220

Leu Thr Thr Gly Thr Ala Gly Gln Ala Leu Glu Thr Leu Gln Val Pro
225                 230                 235                 240

Arg Thr Pro Arg Pro Gly Met Glu Ser Ala Asp Ser Arg Arg Leu Ala
                245                 250                 255

Thr Lys His Ser Arg Lys Ala Leu Lys Ala Ser Leu Thr Leu Gly Ile
            260                 265                 270

Leu Leu Gly Met Phe Phe Val Thr Trp Leu Pro Phe Phe Val Ala Asn
        275                 280                 285

Ile Ala Gln
    290

<210> SEQ ID NO 11
<211> LENGTH: 146
<212> TYPE: PRT
<213> ORGANISM: Rat

<400> SEQUENCE: 11

Ala Val Cys Asp Cys Ile Ser Pro Gly Leu Phe Asp Val Leu Thr Trp
1               5                   10                  15

Leu Gly Tyr Cys Asn Ser Thr Met Asn Pro Ile Ile Tyr Pro Leu Phe
            20                  25                  30

Met Arg Asp Phe Lys Arg Ala Leu Gly Arg Phe Leu His Ala Ser Thr
        35                  40                  45

Val Pro Arg Ser Thr Gly Gln Pro Cys Leu Pro Leu His Val Asp Leu
    50                  55                  60

Ser Gln Arg Cys Gln Thr Arg Pro Gln Leu Gln Gln Val Leu Ala Leu
65                  70                  75                  80

Pro Leu Pro Pro Asn Ser Asp Ser Asp Ser Ala Ser Gly Gly Thr Ser
                85                  90                  95

Gly Leu Gln Leu Thr Ala Gln Leu Leu Leu Pro Gly Glu Ala Thr Arg
            100                 105                 110

Asp Pro Pro Pro Thr Arg Ala Thr Thr Val Val Asn Phe Phe Val
        115                 120                 125

Thr Asp Ser Val Glu Pro Glu Ile Arg Pro His Pro Leu Ser Ser Pro
    130                 135                 140

Val Asn
145

<210> SEQ ID NO 12
<211> LENGTH: 1647
<212> TYPE: DNA
<213> ORGANISM: Homo sapiens
<220> FEATURE:
<221> NAME/KEY: CDS
<222> LOCATION: (135)...(1454)
<221> NAME/KEY: misc_feature
<222> LOCATION: (1)...(1647)
<223> OTHER INFORMATION: n = A,T,C or G

<400> SEQUENCE: 12
actcacctcc cccgggggc gtggtgagtc gcggtctgtt ctcacgacgg tccccgtcca      60
gcctgcggtt cgccgggcc ctcatctgct ttccgccac ctatcactc ccttgccgtc      120 cacccctcggt cctc atg gtc cca gag ccg ggc cca acc gcc aat agc acc    170
              Met Val Pro Glu Pro Gly Pro Thr Ala Asn Ser Thr -continued

```
           1               5                    10
ccg gcc tgg ggg gca ggc gcc cgt cgn nng ggg ggc agc ggc tgg gtg        218
Pro Ala Trp Gly Ala Gly Ala Arg Arg Xaa Gly Gly Ser Gly Trp Val
             15                  20                  25 gcg gcc ggc ctg tgc gtg gtc atc gcg ctg acg gcg gcg gcc aac tcg        266
Ala Ala Gly Leu Cys Val Val Ile Ala Leu Thr Ala Ala Ala Asn Ser
     30                  35                  40 ctg ctg atc gcg ctc atc tgc act cag ccc gcg ctg cgc aac acg tcc        314
Leu Leu Ile Ala Leu Ile Cys Thr Gln Pro Ala Leu Arg Asn Thr Ser
 45                  50                  55                  60 aac ttc ttc ctg gtg tcg ctc ttc acg tct gac ctg atg gtc ggg ctg        362
Asn Phe Phe Leu Val Ser Leu Phe Thr Ser Asp Leu Met Val Gly Leu
                 65                  70                  75 gtg gtg atg ccg ccg gcc atg ctg aac gcg ctg tac ggg cgc tgg gtg        410
Val Val Met Pro Pro Ala Met Leu Asn Ala Leu Tyr Gly Arg Trp Val
             80                  85                  90 ctg gcg cgc ggc ctc tgc ctg ctc tgg acc gcc ttc gac gtg atg tgc        458
Leu Ala Arg Gly Leu Cys Leu Leu Trp Thr Ala Phe Asp Val Met Cys
         95                  100                 105 tgc agc gcc tcc atc ctc aac ctc tgc ctc atc agc ctg gac cgc tac        506
Cys Ser Ala Ser Ile Leu Asn Leu Cys Leu Ile Ser Leu Asp Arg Tyr
 110                 115                 120 ctg ctc atc ctc tcg ccg ctg cgc tac aag ctg cgc atg acg ccc ctg        554
Leu Leu Ile Leu Ser Pro Leu Arg Tyr Lys Leu Arg Met Thr Pro Leu
 125                 130                 135                 140 cgt gcc ctg gcc cta gtc ctg ggc ggc tgg agc ctc gcc gct ctc gcc        602
Arg Ala Leu Ala Leu Val Leu Gly Gly Trp Ser Leu Ala Ala Leu Ala
             145                 150                 155 tcc ttc ctg ccc ctg ctg ctg ggc tgg cac gag ctg ggc cac gca cgg        650
Ser Phe Leu Pro Leu Leu Leu Gly Trp His Glu Leu Gly His Ala Arg
         160                 165                 170 cca ccc gtc cct ggc cag tgc cgc ctg ctg gcc agc ctg cct ttt gtc        698
Pro Pro Val Pro Gly Gln Cys Arg Leu Leu Ala Ser Leu Pro Phe Val
     175                 180                 185 ctt gtg gcg tcg ggc ctc acc ttc ttc ctg ccc tcg ggt gcc ata tgc        746
Leu Val Ala Ser Gly Leu Thr Phe Phe Leu Pro Ser Gly Ala Ile Cys
 190                 195                 200 ttc acc tac tgc agg atc ctg cta gct gcc cgc aag cag gcc gtg cag        794
Phe Thr Tyr Cys Arg Ile Leu Leu Ala Ala Arg Lys Gln Ala Val Gln
 205                 210                 215                 220 gtg gcc tcc ctc acc acc ggc atg gcc agt cag gcc tcg gag acg ctg        842
Val Ala Ser Leu Thr Thr Gly Met Ala Ser Gln Ala Ser Glu Thr Leu
             225                 230                 235 cag gta ccc agg agc cca gcg gca ggg gtg gag tct gct gac agc agg        890
Gln Val Pro Arg Ser Pro Ala Ala Gly Val Glu Ser Ala Asp Ser Arg
         240                 245                 250 cgt cta gca acg aag agc agc agg aag ggc ctg aag gcc agc atg acg        938
Arg Leu Ala Thr Lys Ser Ser Arg Lys Gly Leu Lys Ala Ser Met Thr
     255                 260                 265 ctg ggc atc ctg ctg ggc atg ttc ttt gtg acc tgg ttg ccc ttc ttt        986
Leu Gly Ile Leu Leu Gly Met Phe Phe Val Thr Trp Leu Pro Phe Phe
 270                 275                 280 gtg gcc aac ata gtc cag gcc gtg tgc gac tgc atc tcc cca ggc ctc       1034
Val Ala Asn Ile Val Gln Ala Val Cys Asp Cys Ile Ser Pro Gly Leu
 285                 290                 295                 300 ttc gat gtc ctc aca tgg ctg ggt tac tgt aac agc acc atg aac ccc       1082
Phe Asp Val Leu Thr Trp Leu Gly Tyr Cys Asn Ser Thr Met Asn Pro
             305                 310                 315 atc atc tac cca ctc ttc atg ctg gac ttc aag cgg gcg ctg ggc agg       1130
```

-continued

```
Ile Ile Tyr Pro Leu Phe Met Leu Asp Phe Lys Arg Ala Leu Gly Arg
            320                 325                 330 ttc ctg cca tgt cca cgc tgt ccc cgg gag ccc agg cca gcc tgg cct        1178
Phe Leu Pro Cys Pro Arg Cys Pro Arg Glu Pro Arg Pro Ala Trp Pro
            335                 340                 345 cgc cat cac tgc gca cct ctc aca gcg gcc ccc ggc ccg gcc tta gcc        1226
Arg His His Cys Ala Pro Leu Thr Ala Ala Pro Gly Pro Ala Leu Ala
        350                 355                 360 tac agc agg tgc tgc cgc tgc ccc tgc cgc cgg act cag att cgg act        1274
Tyr Ser Arg Cys Cys Arg Cys Pro Cys Arg Arg Thr Gln Ile Arg Thr
365                 370                 375                 380 cag acg cag gct cag gcg gct cct cgg gcg tgc ggc tca cgg ccc agc        1322
Gln Thr Gln Ala Gln Ala Ala Pro Arg Ala Cys Gly Ser Arg Pro Ser
                385                 390                 395 tgc tgc ttc ctg gcg agg cca ccc agg acc ccc cgc tgc cca cca ggg        1370
Cys Cys Phe Leu Ala Arg Pro Pro Arg Thr Pro Arg Cys Pro Pro Gly
            400                 405                 410 ccg ctg ccg ccg tca att tct tca aca tcg sac ccc gcg gag ccc gag        1418
Pro Leu Pro Pro Ser Ile Ser Ser Thr Ser Xaa Pro Ala Glu Pro Glu
            415                 420                 425 ctg cgg ccg cat cca ctt ggc atc ccc acg aac tga cccggcttgg             1464
Leu Arg Pro His Pro Leu Gly Ile Pro Thr Asn  *
        430                 435 ggctggccaa tggggagctg gattgagcag aacccagacc ctgagtcctt gggccagctc      1524
ttggctaaga ccaggaggct gcaagtctcc tagaagccct ctgagctcca gaggggtgcg      1584
gcagagctga cccctgctg ccatctccag gccccttacc tgcagggatc atagctgact       1644
aga                                                                    1647

<210> SEQ ID NO 13
<211> LENGTH: 439
<212> TYPE: PRT
<213> ORGANISM: Homo sapiens
<220> FEATURE:
<221> NAME/KEY: VARIANT
<222> LOCATION: (1)...(439)
<223> OTHER INFORMATION: Xaa = Any Amino Acid

<400> SEQUENCE: 13

Met Val Pro Glu Pro Gly Pro Thr Ala Asn Ser Thr Pro Ala Trp Gly
 1               5                  10                  15

Ala Gly Ala Arg Xaa Xaa Gly Gly Ser Gly Trp Val Ala Ala Gly Leu
            20                  25                  30

Cys Val Val Ile Ala Leu Thr Ala Ala Ala Asn Ser Leu Leu Ile Ala
        35                  40                  45

Leu Ile Cys Thr Gln Pro Ala Leu Arg Asn Thr Ser Asn Phe Phe Leu
    50                  55                  60

Val Ser Leu Phe Thr Ser Asp Leu Met Val Gly Leu Val Val Met Pro
65                  70                  75                  80

Pro Ala Met Leu Asn Ala Leu Tyr Gly Arg Trp Val Leu Ala Arg Gly
                85                  90                  95

Leu Cys Leu Leu Trp Thr Ala Phe Asp Val Met Cys Cys Ser Ala Ser
            100                 105                 110

Ile Leu Asn Leu Cys Leu Ile Ser Leu Asp Arg Tyr Leu Leu Ile Leu
        115                 120                 125

Ser Pro Leu Arg Tyr Lys Leu Arg Met Thr Pro Leu Arg Ala Leu Ala
    130                 135                 140

Leu Val Leu Gly Gly Trp Ser Leu Ala Ala Leu Ala Ser Phe Leu Pro
```

-continued

```
            145                 150                 155                 160
Leu Leu Leu Gly Trp His Glu Leu Gly His Ala Arg Pro Pro Val Pro
                165                 170                 175

Gly Gln Cys Arg Leu Leu Ala Ser Leu Pro Phe Val Leu Val Ala Ser
            180                 185                 190

Gly Leu Thr Phe Phe Leu Pro Ser Gly Ala Ile Cys Phe Thr Tyr Cys
            195                 200                 205

Arg Ile Leu Leu Ala Ala Arg Lys Gln Ala Val Gln Val Ala Ser Leu
            210                 215                 220

Thr Thr Gly Met Ala Ser Gln Ala Ser Glu Thr Leu Gln Val Pro Arg
225                 230                 235                 240

Ser Pro Ala Ala Gly Val Glu Ser Ala Asp Ser Arg Arg Leu Ala Thr
                245                 250                 255

Lys Ser Ser Arg Lys Gly Leu Lys Ala Ser Met Thr Leu Gly Ile Leu
                260                 265                 270

Leu Gly Met Phe Phe Val Thr Trp Leu Pro Phe Phe Val Ala Asn Ile
            275                 280                 285

Val Gln Ala Val Cys Asp Cys Ile Ser Pro Gly Leu Phe Asp Val Leu
            290                 295                 300

Thr Trp Leu Gly Tyr Cys Asn Ser Thr Met Asn Pro Ile Ile Tyr Pro
305                 310                 315                 320

Leu Phe Met Leu Asp Phe Lys Arg Ala Leu Gly Arg Phe Leu Pro Cys
                325                 330                 335

Pro Arg Cys Pro Arg Glu Pro Arg Pro Ala Trp Pro Arg His His Cys
                340                 345                 350

Ala Pro Leu Thr Ala Ala Pro Gly Pro Ala Leu Ala Tyr Ser Arg Cys
                355                 360                 365

Cys Arg Cys Pro Cys Arg Arg Thr Gln Ile Arg Thr Gln Thr Gln Ala
            370                 375                 380

Gln Ala Ala Pro Arg Ala Cys Gly Ser Arg Pro Ser Cys Cys Phe Leu
385                 390                 395                 400

Ala Arg Pro Pro Arg Thr Pro Arg Cys Pro Pro Gly Pro Leu Pro Pro
                405                 410                 415

Ser Ile Ser Ser Thr Ser Xaa Pro Ala Glu Pro Glu Leu Arg Pro His
                420                 425                 430

Pro Leu Gly Ile Pro Thr Asn
            435
```